US011503986B2

(12) United States Patent
Ye et al.

(10) Patent No.: US 11,503,986 B2
(45) Date of Patent: Nov. 22, 2022

(54) ROBOTIC SYSTEMS AND METHODS FOR NAVIGATION OF LUMINAL NETWORK THAT DETECT PHYSIOLOGICAL NOISE

(71) Applicant: Auris Health, Inc., Redwood City, CA (US)

(72) Inventors: Menglong Ye, Mountain View, CA (US); Ritwik Ummalaneni, San Mateo, CA (US); Hedyeh Rafii-Tari, Mountain View, CA (US); David Paul Noonan, San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/425,069

(22) Filed: May 29, 2019

(65) Prior Publication Data

US 2019/0365209 A1    Dec. 5, 2019

Related U.S. Application Data

(60) Provisional application No. 62/678,520, filed on May 31, 2018.

(51) Int. Cl.
*A61B 1/00* (2006.01)
*G06T 7/55* (2017.01)
(Continued)

(52) U.S. Cl.
CPC ...... *A61B 1/00149* (2013.01); *A61B 1/00009* (2013.01); *A61B 1/00048* (2013.01);
(Continued)

(58) Field of Classification Search
CPC ............ A61B 1/00149; A61B 1/00009; A61B 1/2676; A61B 1/00048; A61B 1/0057;
(Continued)

(56) References Cited

U.S. PATENT DOCUMENTS 4,745,908 A   5/1988  Wardle
5,273,025 A   12/1993 Sakiyam et al.
(Continued)

FOREIGN PATENT DOCUMENTS

CN   101147676   3/2008
CN   101222882   7/2008
(Continued)

OTHER PUBLICATIONS

Anant et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.
(Continued)

*Primary Examiner* — Alexandra L Newton
(74) *Attorney, Agent, or Firm* — Chang & Hale LLP

(57) ABSTRACT

Provided are robotic systems and methods for navigation of luminal network that detect physiological noise. In one aspect, the system includes a set of one or more processors configured to receive first and second image data from an image sensor located on an instrument, detect a set of one or more points of interest the first image data, and identify a set of first locations and a set of second location respectively corresponding to the set of points in the first and second image data. The set of processors are further configured to, based on the set of first locations and the set of second locations, detect a change of location of the instrument within a luminal network caused by movement of the luminal network relative to the instrument based on the set of first locations and the set of second locations.

30 Claims, 27 Drawing Sheets

(51) Int. Cl.
  *G06T 7/262* (2017.01)
  *G06T 7/246* (2017.01)
  *A61B 1/005* (2006.01)
  *A61B 34/00* (2016.01)
  *A61B 5/06* (2006.01)
  *A61B 1/267* (2006.01)
  *A61B 5/00* (2006.01)
  *G06T 7/73* (2017.01)

(52) U.S. Cl.
  CPC .......... *A61B 1/0057* (2013.01); *A61B 1/2676* (2013.01); *A61B 5/062* (2013.01); *A61B 5/7285* (2013.01); *A61B 34/74* (2016.02); *G06T 7/248* (2017.01); *G06T 7/262* (2017.01); *G06T 7/55* (2017.01); *G06T 7/74* (2017.01); *A61B 2034/742* (2016.02); *G06T 2207/10068* (2013.01); *G06T 2207/30061* (2013.01)

(58) Field of Classification Search
  CPC .......... A61B 5/06; A61B 5/061; A61B 5/065; A61B 5/066; A61B 5/067; A61B 5/068; A61B 5/7285; A61B 5/062; A61B 34/30; A61B 34/32; A61B 34/70; A61B 34/71; A61B 34/74; A61B 2034/301; A61B 2034/302; A61B 2034/303; A61B 2034/304; A61B 2034/742; A61B 2034/2046; A61B 2034/2065; A61B 2034/2061; A61B 8/4245; A61B 8/4254; A61B 8/4218; A61B 8/4263; A61B 34/20; A61B 2034/105; A61B 2034/107; A61B 2017/00699; A61B 34/10; G06T 7/74; G06T 7/248; G06T 7/262; G06T 7/55; G06T 2207/30061; G06T 2207/10068
  See application file for complete search history.

(56) References Cited

U.S. PATENT DOCUMENTS

| | | | |
|---|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,454,776 B1 | 9/2002 | Tajima et al. |
| 6,466,198 B1 | 10/2002 | Feinstein |
| 6,490,467 B1 | 12/2002 | Bucholz |
| 6,553,251 B1 | 4/2003 | Lahdesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,697,972 B2 | 4/2010 | Verard et al. |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,084,623 B2 | 7/2015 | Gomez et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State |
| 10,285,574 B2 | 5/2019 | Landey et al. |
| 10,299,870 B2 | 5/2019 | Connolly et al. |
| 10,524,866 B2 | 1/2020 | Srinivasan |
| 10,639,114 B2 | 5/2020 | Schuh et al. |
| 10,667,875 B2 | 6/2020 | DeFonzo |
| 10,743,751 B2 | 8/2020 | Landey et al. |
| 10,751,140 B2 | 8/2020 | Wallace et al. |
| 10,765,487 B2 | 9/2020 | Ho |
| 10,779,898 B2 | 9/2020 | Hill |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |

(56) References Cited

U.S. PATENT DOCUMENTS

| | | |
|---|---|---|
| 10,973,422 B2 | 4/2021 | Pantelopoulos et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbuch |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa |
| 2008/0275349 A1* | 11/2008 | Halperin ............. A61B 5/0205 600/484 |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0080415 A1 | 4/2010 | Qureshi et al. |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0174178 A1 | 7/2010 | Edwards et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0019878 A1 | 1/2011 | Soubelet et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Holsing et al. |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1* | 4/2012 | Higgins ............. A61B 1/00147 382/128 |
| 2012/0120305 A1* | 5/2012 | Takahashi .......... H04N 5/23203 348/352 |
| 2012/0165656 A1 | 6/2012 | Montag |
| 2012/0172712 A1 | 7/2012 | Bar-Tal |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |

(56) References Cited

U.S. PATENT DOCUMENTS

| | | |
|---|---|---|
| 2014/0107390 A1 | 4/2014 | Brown |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357953 A1 | 12/2014 | Roelle et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2014/0379000 A1 | 12/2014 | Romo et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0101442 A1 | 4/2015 | Romo et al. |
| 2015/0119638 A1 | 4/2015 | Yu et al. |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265368 A1* | 9/2015 | Chopra ............... A61B 5/7425 600/424 |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0184032 A1* | 6/2016 | Romo .................. B25J 13/085 606/130 |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0065364 A1 | 3/2017 | Schuh et al. |
| 2017/0065365 A1 | 3/2017 | Schuh |
| 2017/0079725 A1 | 3/2017 | Hoffman |
| 2017/0079726 A1 | 3/2017 | Hoffman |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360418 A1 | 12/2017 | Wong et al. |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0055583 A1 | 3/2018 | Schuh et al. |
| 2018/0098690 A1* | 4/2018 | Iwaki ................. G02B 23/2407 |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1* | 8/2018 | Donhowe ............ A61B 1/0016 |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1* | 2/2019 | Abhari ................ A61B 90/361 |
| 2019/0083183 A1 | 3/2019 | Moll et al. |
| 2019/0086349 A1 | 3/2019 | Nelson |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0125164 A1 | 5/2019 | Roelle et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |

(56) References Cited

U.S. PATENT DOCUMENTS

| | | |
|---|---|---|
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1* | 9/2019 | Michihata ............ G06T 7/0012 |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker et al. |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105511881 A | 4/2016 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3 025 630 | 6/2016 |
| JP | 2001000448 A | 1/2001 |
| JP | 2016529062 A | 9/2016 |
| KR | 10-2014-0009359 | 1/2014 |
| RU | 2569699 C2 | 11/2015 |
| WO | WO 05/087128 | 9/2005 |
| WO | 2006051523 A2 | 5/2006 |
| WO | WO 09/097461 | 6/2007 |
| WO | WO 15/089013 | 6/2015 |
| WO | WO 16/077419 | 5/2016 |
| WO | WO 17/036774 | 3/2017 |
| WO | WO 17/048194 | 3/2017 |
| WO | WO 17/066108 | 4/2017 |
| WO | 2017081821 A1 | 5/2017 |
| WO | WO 17/146890 | 8/2017 |
| WO | WO 17/167754 | 10/2017 |

OTHER PUBLICATIONS

Ciuti et al., 2012, Intra-operative monocular 30 reconstruction for image-guided navigation in active locomotion capsule endoscopy. Biomedical Robotics And Biomechatronics (Biorob), 4th IEEE Ras & Embs International Conference On IEEE.

Fallavollita et al., 2010, Acquiring multiview C-arm images to assist cardiac ablation procedures, EURASIP Journal on Image and Video Processing, vol. 2010, Article ID 871408, pp. 1-10.

Haigron et al., 2004, Depth-map-based scene analysis for active navigation in virtual angioscopy, IEEE Transactions on Medical Imaging, 23(11):1380-1390.

Konen et al., 1998, The VN-project: endoscopic image processing for neurosurgery, Computer Aided Surgery, 3:1-6.

Kumar et al., 2014, Stereoscopic visualization of laparoscope image using depth information from 3D model, Computer methods and programs in biomedicine 113(3):862-868.

Livatino et al., 2015, Stereoscopic visualization and 3-D technologies in medical endoscopic teleoperation, IEEE.

Luo et al., 2010, Modified hybrid bronchoscope tracking based on sequential monte carlo sampler: Dynamic phantom validation, Asian Conference on Computer Vision. Springer, Berlin, Heidelberg.

Mayo Clinic, Robotic Surgery, https://www.mayoclinic.org/tests-procedures/robotic-surgery/about/pac-20394974?p=1, downloaded from the Internet on Jul. 12, 2018, 2 pp.

Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.

Nadeem et al., 2016, Depth Reconstruction and Computer-Aided Polyp Detection in Optical Colonoscopy Video Frames, arXiv preprint arXiv:1609.01329.

Point Cloud, Sep. 10, 2010, Wikipedia, 2 pp.

Racadio et al., Dec. 2007, Live 3D guidance in the interventional radiology suite, AJR, 189:W357-W364.

Sato et al., 2016, Techniques of stapler-based navigational thoracoscopic segmentectomy using virtual assisted lung mapping (VAL-MAP), Journal of Thoracic Disease, 8(Suppl 9):S716.

Shen et al., 2015, Robust camera localisation with depth reconstruction for bronchoscopic navigation. International Journal of Computer Assisted Radiology and Surgery, 10(6):801-813.

(56) References Cited

OTHER PUBLICATIONS

Shi et al., Sep. 14-18, 2014, Simultaneous catheter and environment modeling for trans-catheter aortic valve implantation, IEEE/RSJ International Conference on Intelligent Robots and Systems, pp. 2024-2029.
Solheim et al., May 14, 2009, Navigated resection of giant intracranial meningiomas based on intraoperative 3D ultrasound, Acta Neurochir, 151:1143-1151.
Song et al., 2012, Autonomous and stable tracking of endoscope instrument tools with monocular camera, Advanced Intelligent Mechatronics (AIM), 2012 IEEE-ASME International Conference on. IEEE.
Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.
Wilson et al., 2008, a buyer's guide to electromagnetic tracking systems for clinical applications, Proc. of SPCI, 6918:69182B-1 p. 6918B-11.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
International search report and written opinion dated Aug. 8, 2019 for PCT/US2019/034304.
Al-Ahmad et al., dated 2005, Early experience with a computerized robotically controlled catheter system, Journal of Interventional Cardiac Electrophysiology, 12:199-202.
Bell et al., 2014, Six DOF motion estimation for teleoperated flexible endoscopes using optical flow: a comparative study, IEEE International Conference on Robotis and Automation.
Gutierrez et al., Mar. 2008, A practical global distortion correction method for an image intensifier based x-ray fluoroscopy system, Med. Phys, 35(3):997-1007.
Hansen Medical, Inc. 2005. System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Marrouche et al., dated May 6, 2005, AB32-1, Preliminary human experience using a novel robotic catheter remote control, Heart Rhythm, 2(5):S63.
Oh et al., dated May 2005, P5-75, Novel robotic catheter remote control system: safety and accuracy in delivering RF Lesions in all 4 cardiac chambers, Heart Rhythm, 2(5):S277-S278.
Reddy et al., May 2005, P1-53. Porcine pulmonary vein ablation using a novel robotic catheter control system and real-time integration of CT imaging with electroanatomical mapping, Hearth Rhythm, 2(5):S121.
Ren et al., 2011, Multisensor data fusion in an integrated tracking systEm for endoscopic surgery, IEEE Transactions on Information Technology in Biomedicine, 16(1):106-111.
Slepian, dated 2010, Robotic Catheter Intervention: the Hansen Medical Sensei Robot Catheter System, PowerPoint presentation, 28 pp.
Solomon et al., Dec. 2000, Three-dimensional CT-Guided Bronchoscopy With a Real-Time Electromagnetic Position Sensor A Comparison of Two Image Registration Methods, Chest, 118(6):1783-1787.
"Mourgues et al., 2002, Flexible calibration of actuated stereoscopic endoscope for overlay inrobotassisted surgery, International Conference on Medical Image Computing and Computer-Assisted Intervention. Sorinqer, Bedin, Heidelberq", 10 pages.
CN office action for appl No. 201880001545, dated Jul. 20, 2021, 8 pages.
CN Office action for appl No. 201880001545, dated Oct. 20, 2020, 30 pages.
EP Search report for appl No. 18778077, dated Jan. 20, 2021,3 page.
EP written opinion for appl No. 18778077, dated Jan. 20, 2021, 4 page.
International Search Report and Written Opinion dated Aug. 8, 2018 in application No. PCT/US18/25218, 15 pages.
Notice of allowance for U.S. Appl. No. 15/939,678, dated Aug. 30, 2021, 5 pages.
Vemuri et al., Dec. 2015, Inter-operative biopsy site relocations in endoluminal surgery, IEEE Transactions on Biomedical Engineering, Institute of Electrical and Electronics Engineers,<10.1109/TBME.2015.2503981>, 13 pages.
Wilson et al., 2008, a buyer's guide to electromagnetic tracking systems for clinical applications, Proc. of SPCI, 6918:691828-1 p 69188-11, 12 pages.
"Mourgues et al., 2002, Flexible calibration of actuated stereoscopic endoscope for oveday inrobotassisted surgery, International Conference on Medical Image Computing and Computer-Assisted Intervention. Springer, Berlin, Heidelberg", 10 pages.
Advisory action for U.S. Appl. No. 15/939,678, dated Aug. 9, 2019, 3 pages.
Advisory action for U.S. Appl. No. 15/939,678, dated Sep. 8, 2020, 3 pages.
Notice of allowance for U.S. Appl. No. 15/939,678, dated Jun. 18, 2021, 8 pages.
Office action for U.S. Appl. No. 15/939,678, dated Feb. 10, 2020,15 pages.
Office action for U.S. Appl. No. 15/939,678, dated Feb. 11, 2019, 6 pages.
Office action for U.S. Appl. No. 15/939,678, dated Feb. 22, 2021, 14 pages.
Office action for U.S. Appl. No. 15/939,678, dated Jun. 29, 2020, 14 pages.
Office action for U.S. Appl. No. 15/939,678, dated Jun. 3, 2019, 14 pages.
Office action for U.S. Appl. No. 15/939,678, dated Oct. 11, 2018, 14 pages.
EP Search Report for appl No. 19810872.2, dated Feb. 4, 2022, 12 pages.
Notice of Allowance for U.S. Appl. No. 15/939,678, dated Dec. 17, 2021, 8 pages.
JP Office Action for Appl. No. 2019553011, dated Mar. 15, 2022,4 pages.
JP Search Report for Appl. No. 2019553011, dated Jan. 13, 2022, 14 pages.
KR Office Action for appl. No. 1020187028219, dated Mar. 31, 2022, 1 page.
Notice of Allowance for U.S. Appl. No. 15/939,678, dated Jun. 20, 2022, 8 pages.

\* cited by examiner

ROBOTIC SYSTEMS AND METHODS FOR NAVIGATION OF LUMINAL NETWORK THAT DETECT PHYSIOLOGICAL NOISE

CROSS-REFERENCE TO RELATED APPLICATION(S)

This application claims the benefit of U.S. Provisional Application No. 62/678,520, filed May 31, 2018, which is hereby incorporated by reference in its entirety.

TECHNICAL FIELD

The systems and methods disclosed herein are directed to surgical robotics, and more particularly to endoluminal navigation.

BACKGROUND

Bronchoscopy is a medical procedure that allows a physician to examine the inside conditions of a patient's lung airways, such as bronchi and bronchioles. The lung airways carry air from the trachea, or windpipe, to the lungs. During the medical procedure, a thin, flexible tubular tool, known as a bronchoscope, may be inserted into the patient's mouth and passed down the patient's throat into his/her lung airways, and patients are generally anesthetized in order to relax their throats and lung cavities for surgical examinations and operations during the medical procedure.

In the related art, a bronchoscope can include a light source and a small camera that allows a physician to inspect a patient's windpipe and airways, and a rigid tube may be used in conjunction with the bronchoscope for surgical purposes, e.g., when there is a significant amount of bleeding in the lungs of the patient or when a large object obstructs the throat of the patient. When the rigid tube is used, the patient is often anesthetized. Robotic bronchoscopes provide tremendous advantages in navigation through tubular networks. They can ease use and allow therapies and biopsies to be administered conveniently even during the bronchoscopy stage.

Apart from mechanical devices or platforms, e.g., robotic bronchoscopes described above, various methods and software models may be used to help with the surgical operations. As an example, a computerized tomography (CT) scan of the patient's lungs is often performed during pre-operation of a surgical examination. Data from the CT scan may be used to generate a three-dimensional (3D) model of airways of the patient's lungs, and the generated 3D model enables a physician to access a visual reference that may be useful during the operative procedure of the surgical examination.

However, previous techniques for navigation of tubular networks still have challenges, even when employing medical devices (e.g., robotic bronchoscopes) and when using existing methods (e.g., performing CT scans and generating 3D models). As one example, motion estimation of a medical device (e.g., a bronchoscope tool) inside a patient's body may not be accurate based on location and orientation change of the device, and as a result the device's position may not be accurately or correctly localized inside the patient's body in real time. Inaccurate location information for such an instrument may provide misleading information to the physician that uses the 3D model as a visual reference during medical operation procedures.

Thus, there is a need for improved techniques for navigating through a network of tubular structures.

SUMMARY

In one aspect, there is provided a medical robotic system, comprising a set of one or more processors; and at least one computer-readable memory in communication with the set of processors and having stored thereon computer-executable instructions to cause the set of processors to: receive first image data from an image sensor located on an instrument, the instrument configured to be driven through a luminal network of a patient, detect a set of one or more points of interest the first image data, identify a set of first locations respectively corresponding to the set of points in the first image data, receive second image data from the image sensor, detect the set of one or more points in the second image data, identify a set of second locations respectively corresponding to the set of points in the second image data, and based on the set of first locations and the set of second locations, detect a change of location of the instrument within the luminal network caused by movement of the luminal network relative to the instrument.

In another aspect, there is provided a non-transitory computer readable storage medium having stored thereon instructions that, when executed, cause at least one computing device to: receive first image data from an image sensor located on an instrument, the instrument configured to be driven through a luminal network of a patient; detect a set of one or more points of interest the first image data; identify a set of first locations respectively corresponding to the set of points in the first image data; receive second image data from the image sensor; detect the set of one or more points in the second image data; identify a set of second locations respectively corresponding to the set of points in the second image data; and based on the set of first locations and the set of second locations, detect a change of location of the instrument within the luminal network caused by movement of the luminal network relative to the instrument.

In yet another aspect, there is provided a method for detecting a change of location of an instrument, comprising: receiving first image data from an image sensor located on the instrument, the instrument configured to be driven through a luminal network of a patient; detecting a set of one or more points of interest the first image data; identifying a set of first locations respectively corresponding to the set of points in the first image data; receiving second image data from the image sensor; detecting the set of one or more points in the second image data; identifying a set of second locations respectively corresponding to the set of points in the second image data; and based on the set of first locations and the set of second locations, detecting the change of location of the instrument within the luminal network caused by movement of the luminal network relative to the instrument.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. Surgical Robotic System

Figure 1A:
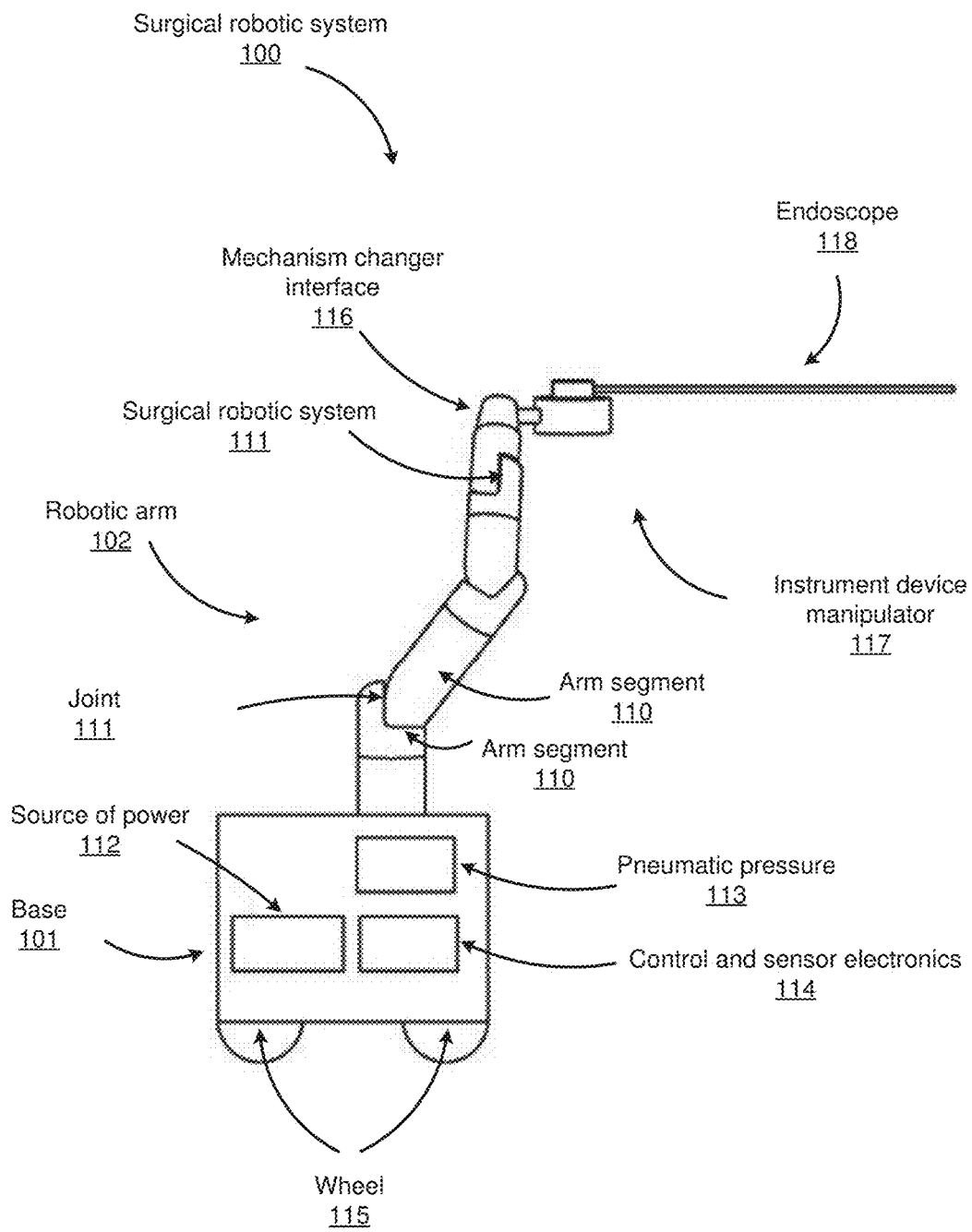
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2 in Section II. Command Console. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
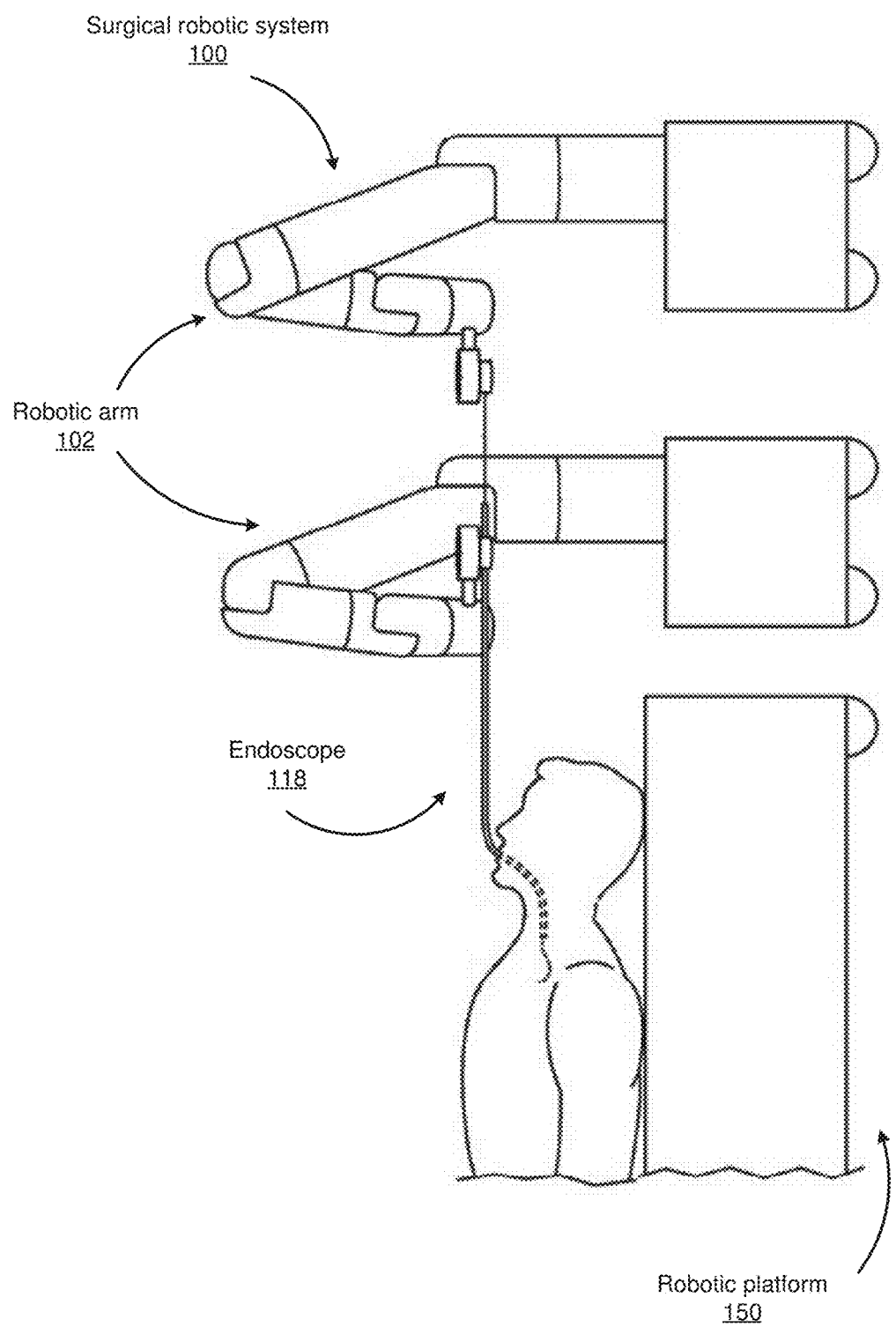
FIGS. 1B-1F show various perspective views of a robotic platform coupled to the surgical robotic system shown in FIG. 1A, according to one embodiment.
Figure 1C:
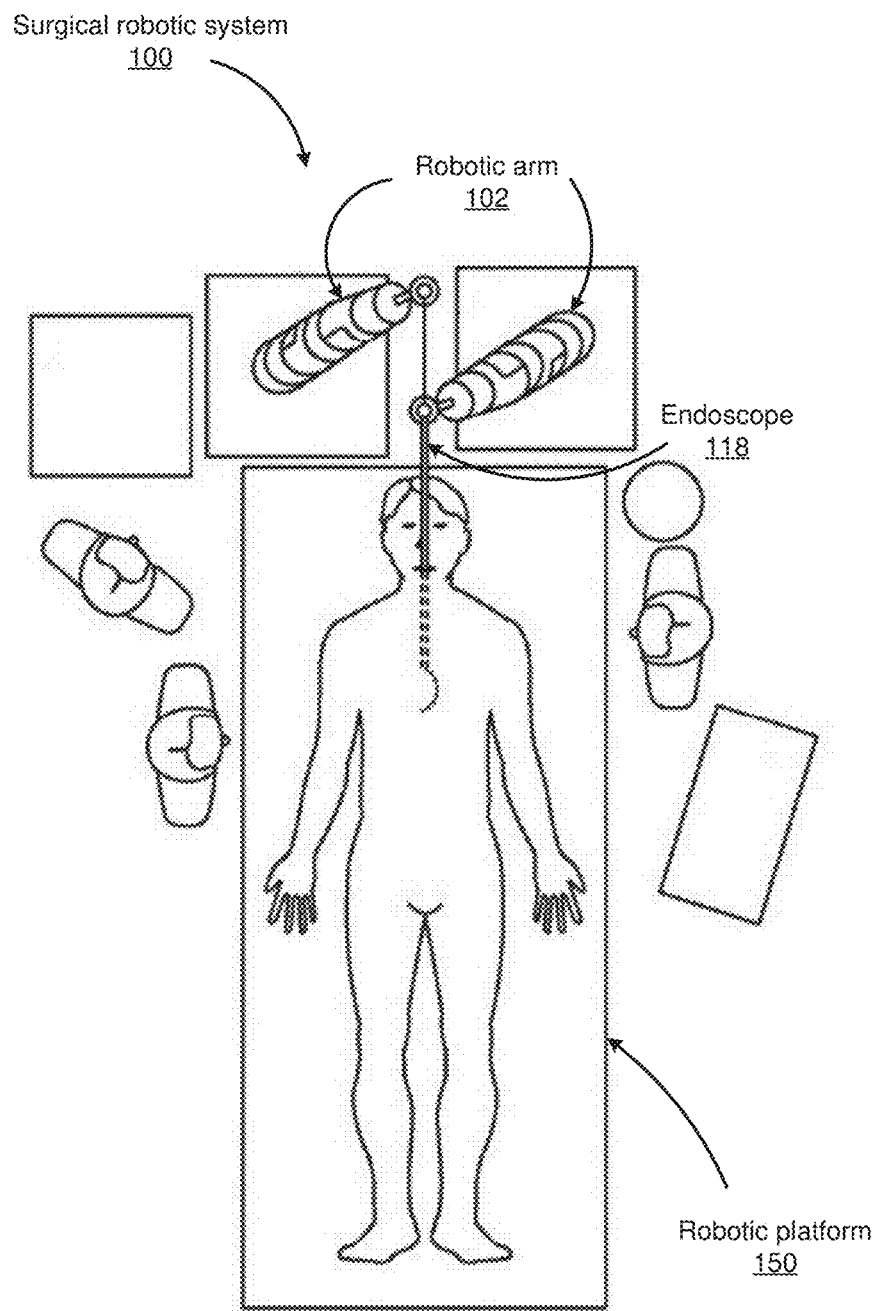
Figure 1D:
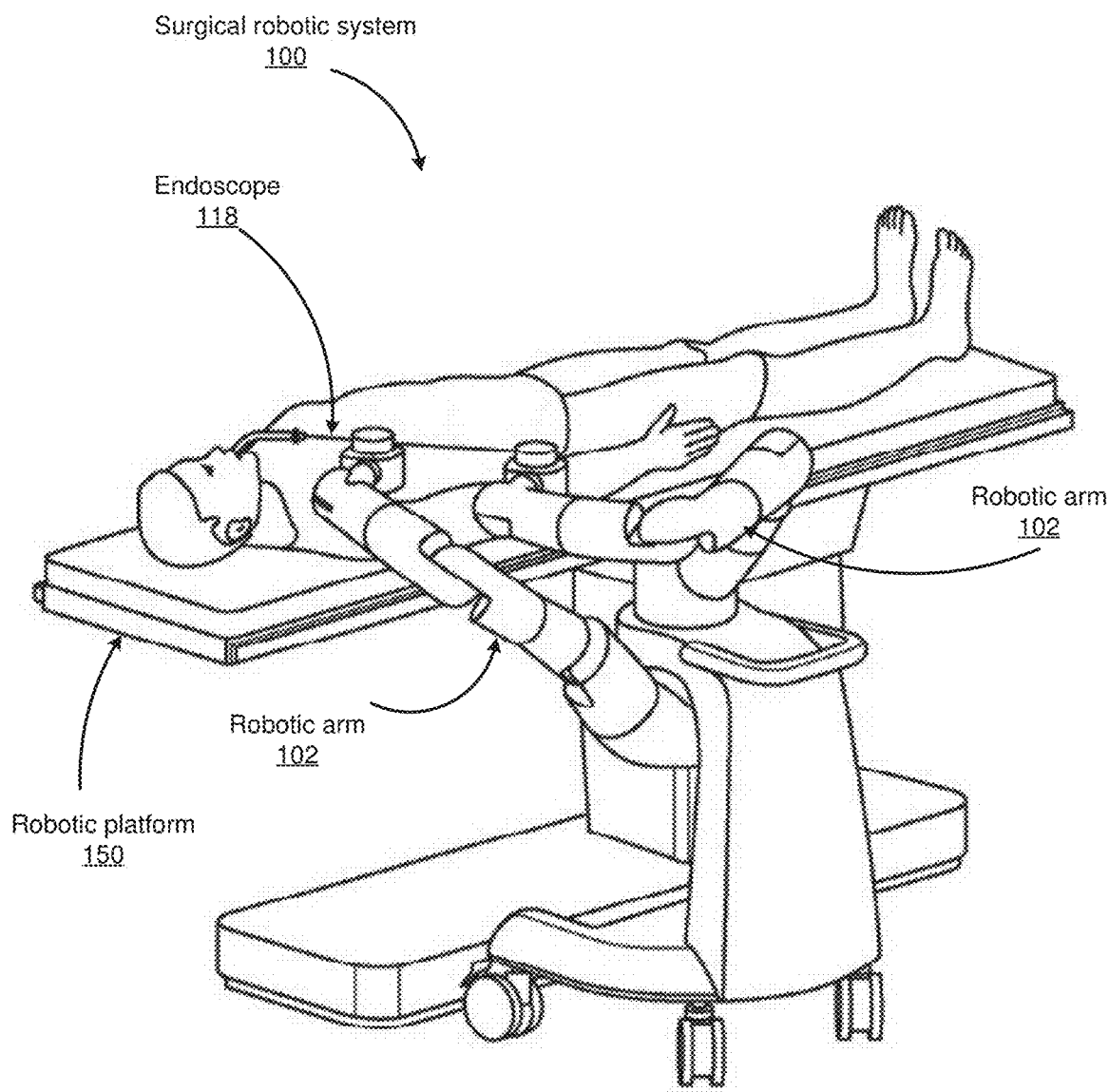
Figure 1E:
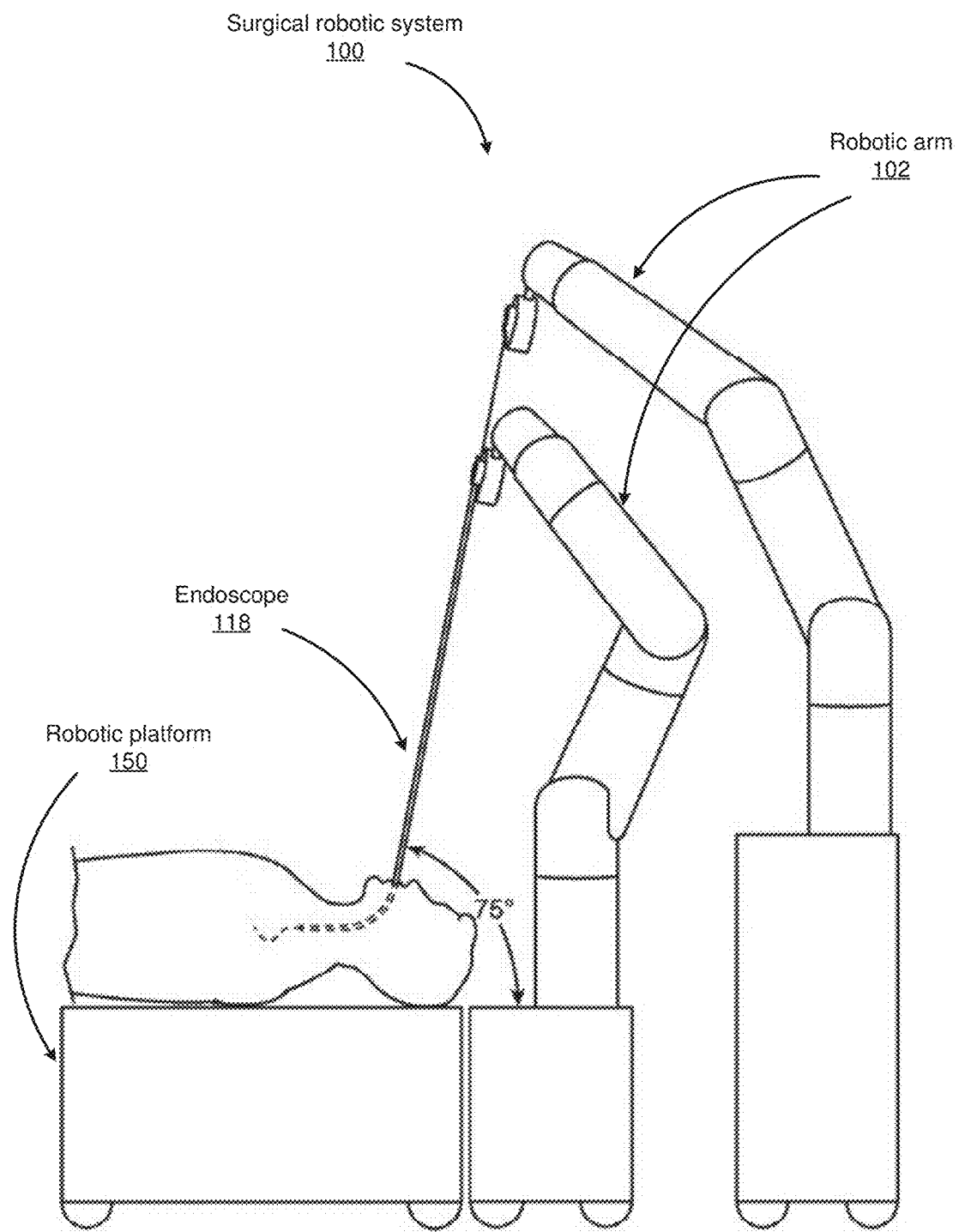
Figure 1F:
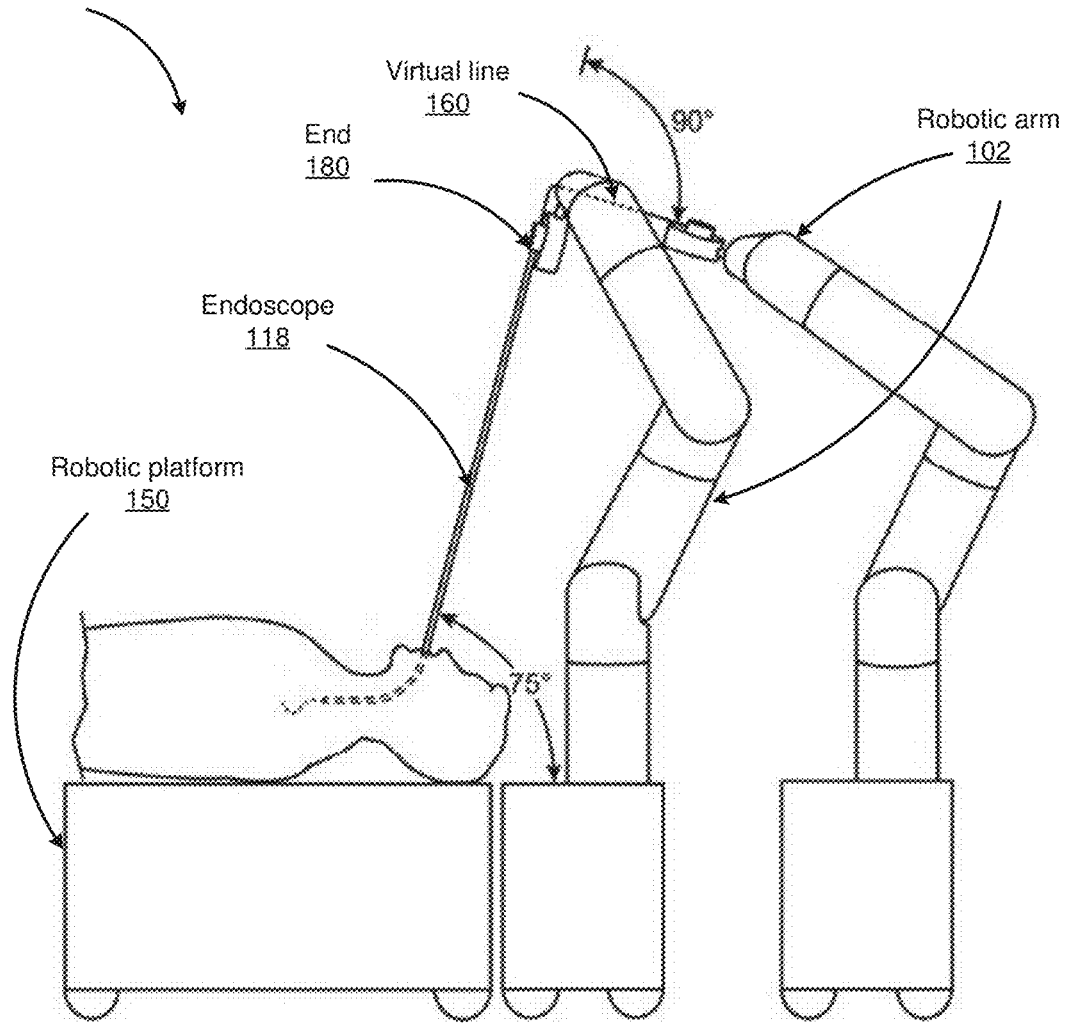

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscopic 118 to insert the endoscopic inside a patient's body, and the patient is lying on the robotic platform 150. FIG. 1C shows a top view of the surgical robotic system 100 and the robotic platform 150, and the endoscopic 118 manipulated by the robotic arms is inserted inside the patient's body. FIG. 1D shows a perspective view of the surgical robotic system 100 and the robotic platform 150, and the endoscopic 118 is controlled to be positioned horizontally parallel with the robotic platform. FIG. 1E shows another perspective view of the surgical robotic system 100 and the robotic platform 150, and the endoscopic 118 is controlled to be positioned relatively perpendicular to the robotic platform. In more detail, in FIG. 1E, the angle between the horizontal surface of the robotic platform 150 and the endoscopic 118 is 75 degree. FIG. 1F shows the perspective view of the surgical robotic system 100 and the robotic platform 150 shown in FIG. 1E, and in more detail, the angle between the endoscopic 118 and the virtual line 160 connecting one end 180 of the endoscopic and the robotic arm 102 that is positioned relatively farther away from the robotic platform is 90 degree.

II. Command Console

Figure 2:
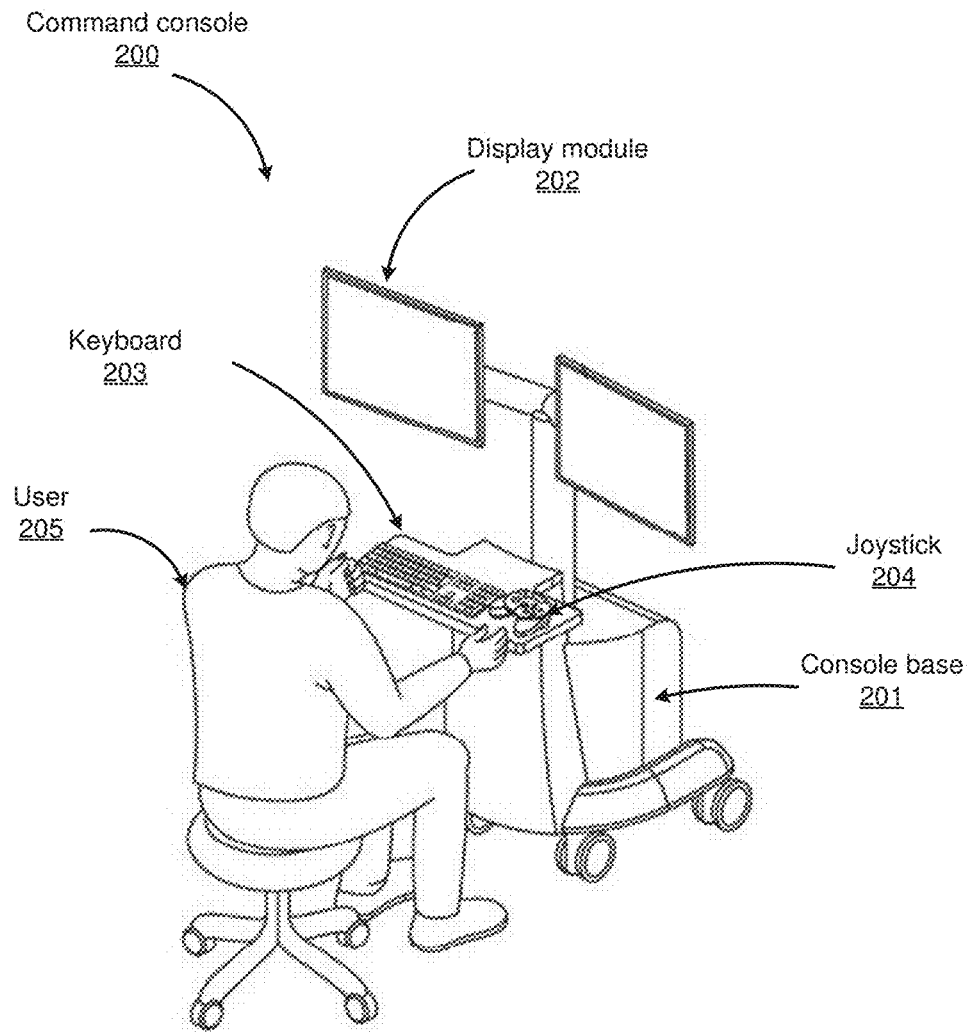
FIG. 2 shows an example command console for the example surgical robotic system, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and scans/images generated based on preoperative model data (e.g., CT scans).

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3A:
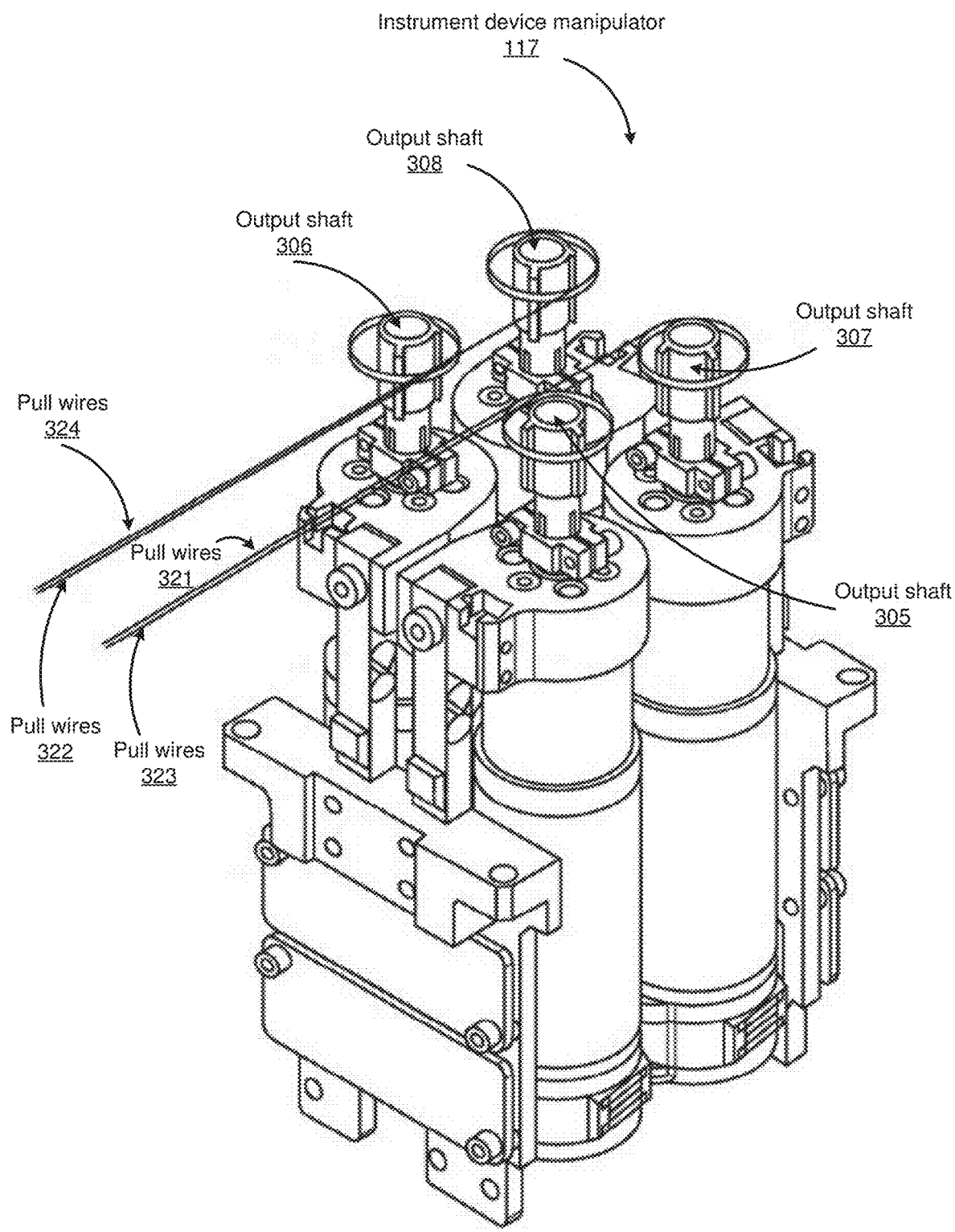
FIG. 3A shows an isometric view of an example independent drive mechanism of the instrument device manipulator (IDM) shown in FIG. 1A, according to one embodiment.

FIG. 3A shows an isometric view of an example independent drive mechanism of the IDM 117 shown in FIG. 1, according to one embodiment. The independent drive mechanism can tighten or loosen the pull wires 321, 322, 323, and 324 (e.g., independently from each other) of an endoscope by rotating the output shafts 305, 306, 307, and 308 of the IDM 117, respectively. Just as the output shafts 305, 306, 307, and 308 transfer force down pull wires 321, 322, 323, and 324, respectively, through angular motion, the pull wires 321, 322, 323, and 324 transfer force back to the output shafts. The IDM 117 and/or the surgical robotic system 100 can measure the transferred force using a sensor, e.g., a strain gauge further described below.

Figure 3B:
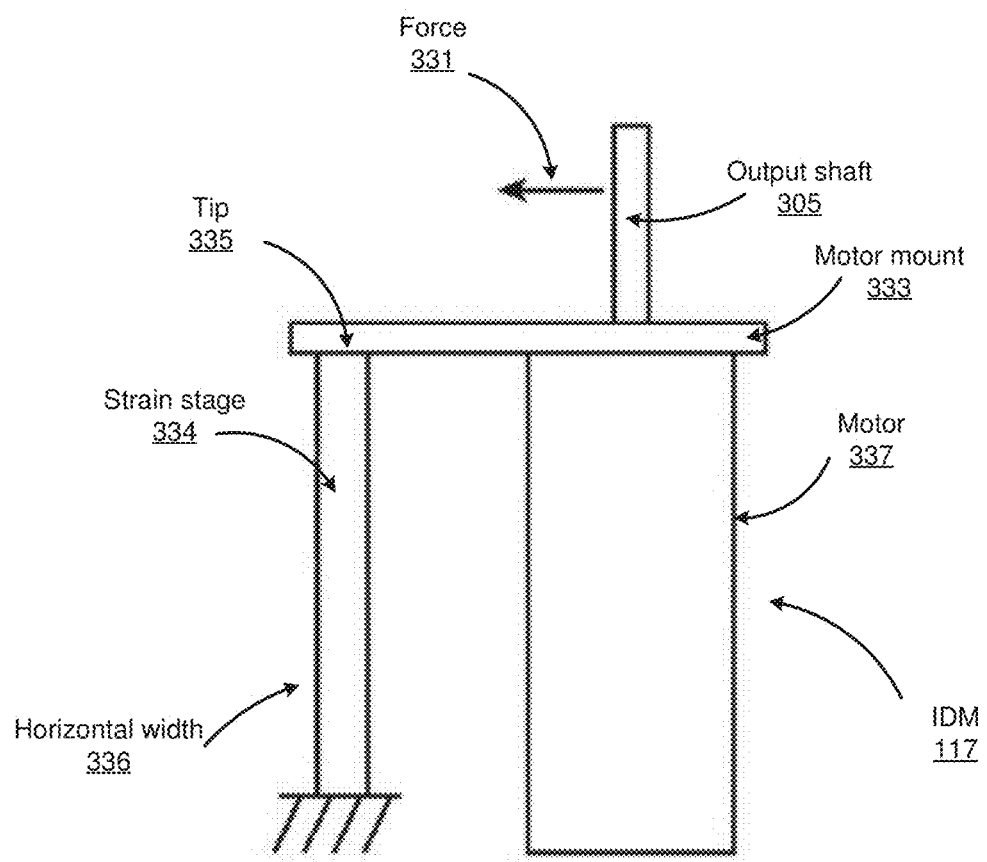
FIG. 3B shows a conceptual diagram that shows how forces may be measured by a strain gauge of the independent drive mechanism shown in FIG. 3A, according to one embodiment.

FIG. 3B shows a conceptual diagram that shows how forces may be measured by a strain gauge 334 of the independent drive mechanism shown in FIG. 3A, according to one embodiment. A force 331 may direct away from the output shaft 305 coupled to the motor mount 333 of the motor 337. Accordingly, the force 331 results in horizontal displacement of the motor mount 333. Further, the strain gauge 334 horizontally coupled to the motor mount 333 experiences strain in the direction of the force 331. The strain may be measured as a ratio of the horizontal displacement of the tip 335 of strain gauge 334 to the overall horizontal width 336 of the strain gauge 334.

In some embodiments, the IDM 117 includes additional sensors, e.g., inclinometers or accelerometers, to determine an orientation of the IDM 117. Based on measurements from the additional sensors and/or the strain gauge 334, the surgical robotic system 100 can calibrate readings from the strain gauge 334 to account for gravitational load effects. For example, if the IDM 117 is oriented on a horizontal side of the IDM 117, the weight of certain components of the IDM 117 may cause a strain on the motor mount 333. Accordingly, without accounting for gravitational load effects, the strain gauge 334 may measure strain that did not result from strain on the output shafts.

IV. Endoscope

Figure 4A:
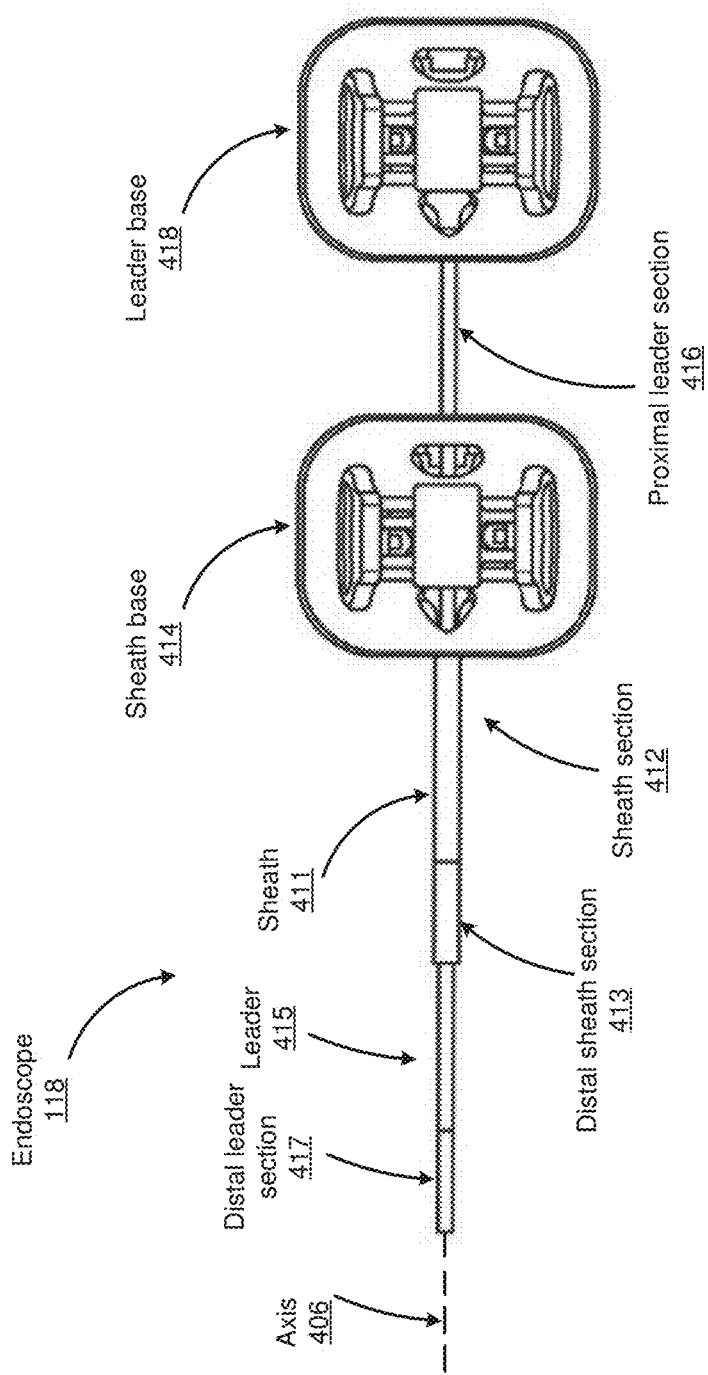
FIG. 4A shows a top view of an example endoscope, according to one embodiment.

FIG. 4A shows a top view of an example endoscope 118, according to one embodiment. The endoscope 118 includes a leader 415 tubular component nested or partially nested inside and longitudinally-aligned with a sheath 411 tubular component. The sheath 411 includes a proximal sheath section 412 and distal sheath section 413. The leader 415 has a smaller outer diameter than the sheath 411 and includes a proximal leader section 416 and distal leader section 417. The sheath base 414 and the leader base 418 actuate the distal sheath section 413 and the distal leader section 417, respectively, for example, based on control signals from a user of a surgical robotic system 100. The sheath base 414 and the leader base 418 are, e.g., part of the IDM 117 shown in FIG. 1.

Both the sheath base 414 and the leader base 418 include drive mechanisms (e.g., the independent drive mechanism further described with reference to FIG. 3A-B in Section III. Instrument Device Manipulator) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, or optical signals from IDMs to the sheath 411 and leader 414, respectively. A pull wire may include a steel coil pipe along the length of the pull wire within the sheath 411 or the leader 415, which transfers axial compression back to the origin of the load, e.g., the sheath base 414 or the leader base 418, respectively.

The endoscope 118 can navigate the anatomy of a patient with ease due to the multiple degrees of freedom provided by pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of motion. The combination of rotational angles and multiple degrees of freedom provides a user of the surgical robotic system 100 with a user friendly and instinctive control of the endoscope 118.

Figure 4B:
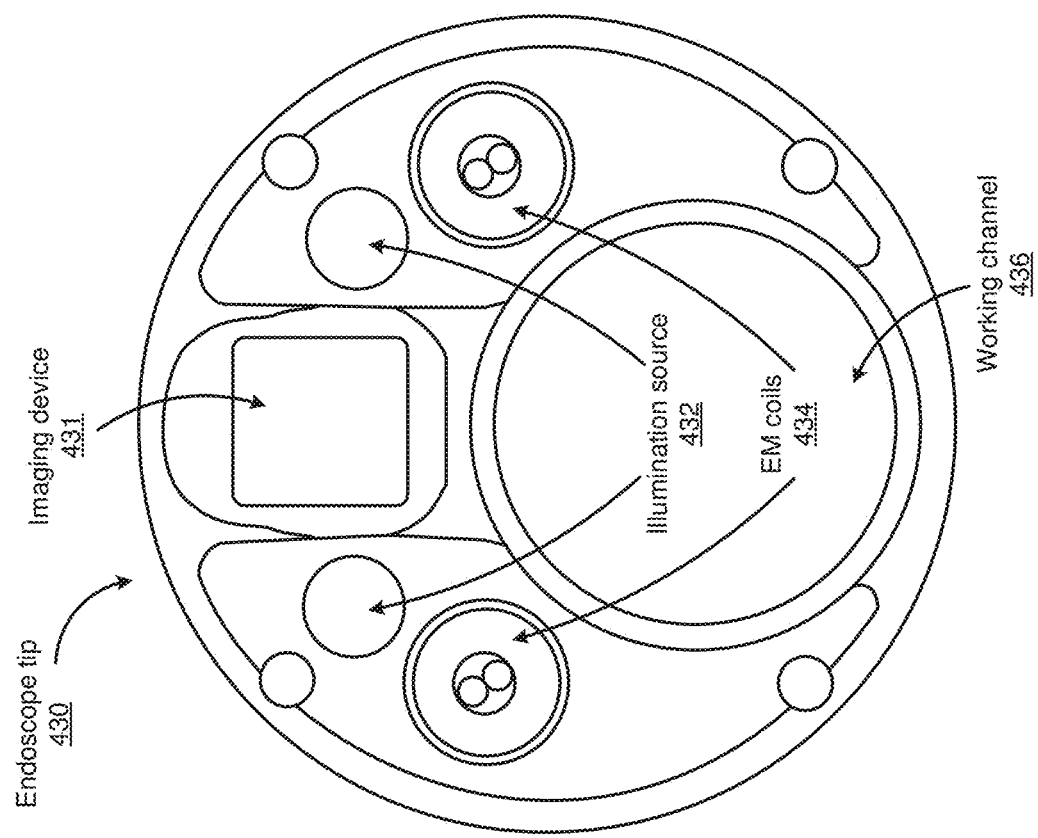
FIG. 4B shows an example endoscope tip of the endoscope shown in FIG. 4A, according to one embodiment.

FIG. 4B illustrates an example endoscope tip 430 of the endoscope 118 shown in FIG. 4A, according to one embodiment. In FIG. 4B, the endoscope tip 430 includes an imaging device 431 (e.g., a camera), illumination sources 432, and ends of EM coils 434. The illumination sources 432 provide light to illuminate an interior portion of an anatomical space.

The provided light allows the imaging device 431 to record images of that space, which can then be transmitted to a computer system such as command console 200 for processing as described herein. Electromagnetic (EM) coils 434 located on the tip 430 may be used with an EM tracking system to detect the position and orientation of the endoscope tip 430 while it is disposed within an anatomical system. In some embodiments, the coils may be angled to provide sensitivity to EM fields along different axes, giving the ability to measure a full 6 degrees of freedom: three positional and three angular. In other embodiments, only a single coil may be disposed within the endoscope tip 430, with its axis oriented along the endoscope shaft of the endoscope 118; due to the rotational symmetry of such a system, it is insensitive to roll about its axis, so only 5 degrees of freedom may be detected in such a case. The endoscope tip 430 further comprises a working channel 436 through which surgical instruments, such as biopsy needles, may be inserted along the endoscope shaft, allowing access to the area near the endoscope tip.

V. Registration Transform of EM System to 3D Model

V. A. Schematic Setup of an EM Tracking System

Figure 5:
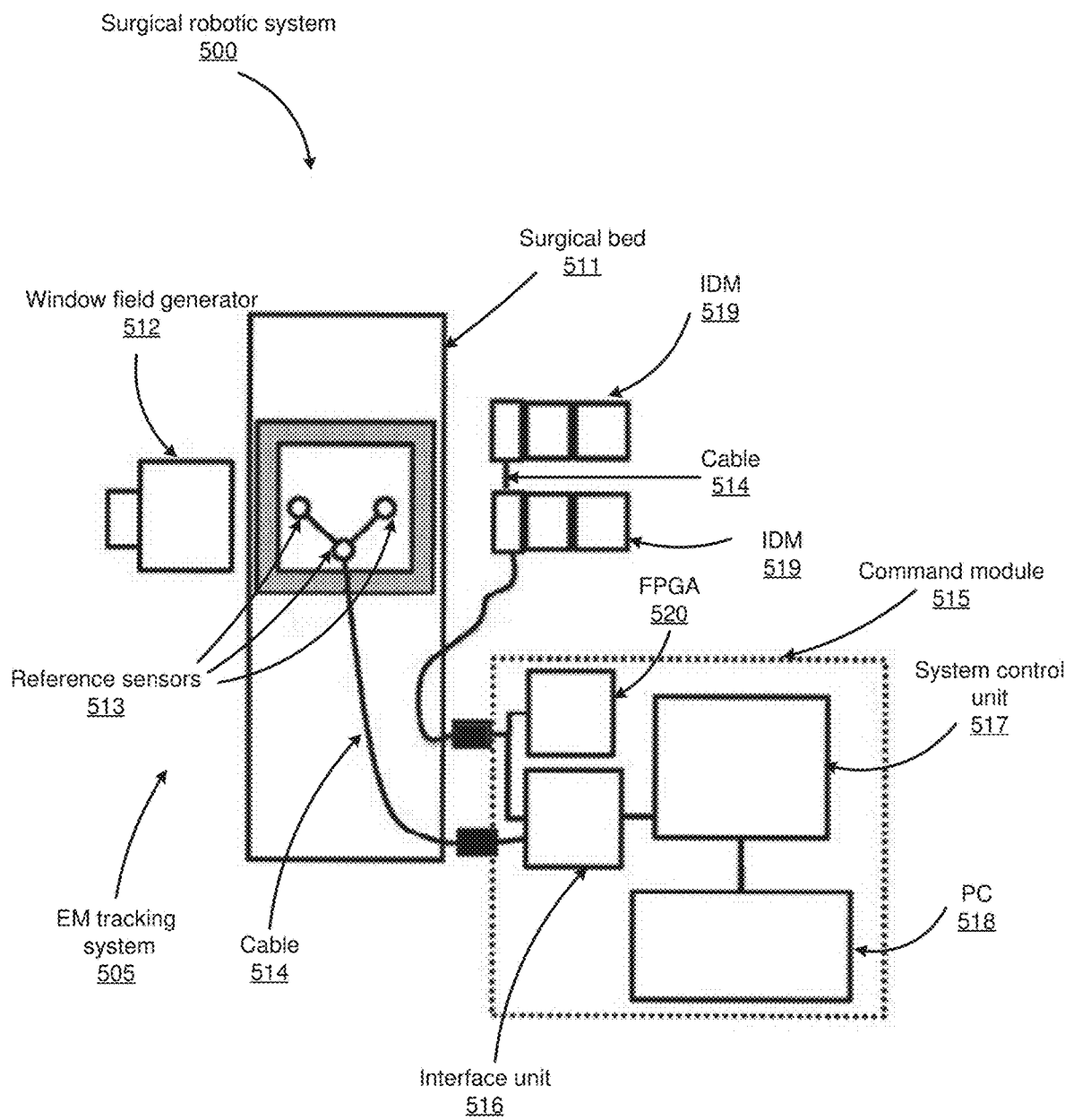
FIG. 5 shows an example schematic setup of an EM tracking system included in a surgical robotic system, according to one embodiment.

FIG. 5 shows an example schematic setup of an EM tracking system 505 included in a surgical robotic system 500, according to one embodiment. In FIG. 5, multiple robot components (e.g., window field generator, reference sensors as described below) are included in the EM tracking system 505. The robotic surgical system 500 includes a surgical bed 511 to hold a patient's body. Beneath the bed 511 is the window field generator (WFG) 512 configured to sequentially activate a set of EM coils (e.g., the EM coils 434 shown in FIG. 4B). The WFG 512 generates an alternating current (AC) magnetic field over a wide volume; for example, in some cases it may create an AC field in a volume of about 0.5×0.5×0.5 m.

Additional fields may be applied by further field generators to aid in tracking instruments within the body. For example, a planar field generator (PFG) may be attached to a system arm adjacent to the patient and oriented to provide an EM field at an angle. Reference sensors 513 may be placed on the patient's body to provide local EM fields to further increase tracking accuracy. Each of the reference sensors 513 may be attached by cables 514 to a command module 515. The cables 514 are connected to the command module 515 through interface units 516 which handle communications with their respective devices as well as providing power. The interface unit 516 is coupled to a system control unit (SCU) 517 which acts as an overall interface controller for the various entities mentioned above. The SCU 517 also drives the field generators (e.g., WFG 512), as well as collecting sensor data from the interface units 516, from which it calculates the position and orientation of sensors within the body. The SCU 517 may be coupled to a personal computer (PC) 518 to allow user access and control.

The command module 515 is also connected to the various IDMs 519 coupled to the surgical robotic system 500 as described herein. The IDMs 519 are typically coupled to a single surgical robotic system (e.g., the surgical robotic system 500) and are used to control and receive data from their respective connected robotic components; for example, robotic endoscope tools or robotic arms. As described above, as an example, the IDMs 519 are coupled to an endoscopic tool (not shown here) of the surgical robotic system 500

The command module 515 receives data passed from the endoscopic tool. The type of received data depends on the corresponding type of instrument attached. For example, example received data includes sensor data (e.g., image data, EM data), robot data (e.g., endoscopic and IDM physical motion data), control data, and/or video data. To better handle video data, a field-programmable gate array (FPGA) 520 may be configured to handle image processing. Comparing data obtained from the various sensors, devices, and field generators allows the SCU 517 to precisely track the movements of different components of the surgical robotic system 500, and for example, positions and orientations of these components.

In order to track a sensor through the patient's anatomy, the EM tracking system 505 may require a process known as "registration," where the system finds the geometric transformation that aligns a single object between different coordinate systems. For instance, a specific anatomical site on a patient has two different representations in the 3D model coordinates and in the EM sensor coordinates. To be able to establish consistency and common language between these two different coordinate systems, the EM tracking system 505 needs to find the transformation that links these two representations, i.e., registration. For example, the position of the EM tracker relative to the position of the EM field generator may be mapped to a 3D coordinate system to isolate a location in a corresponding 3D model.

V. B. 3D Model Representation

Figure 6A:
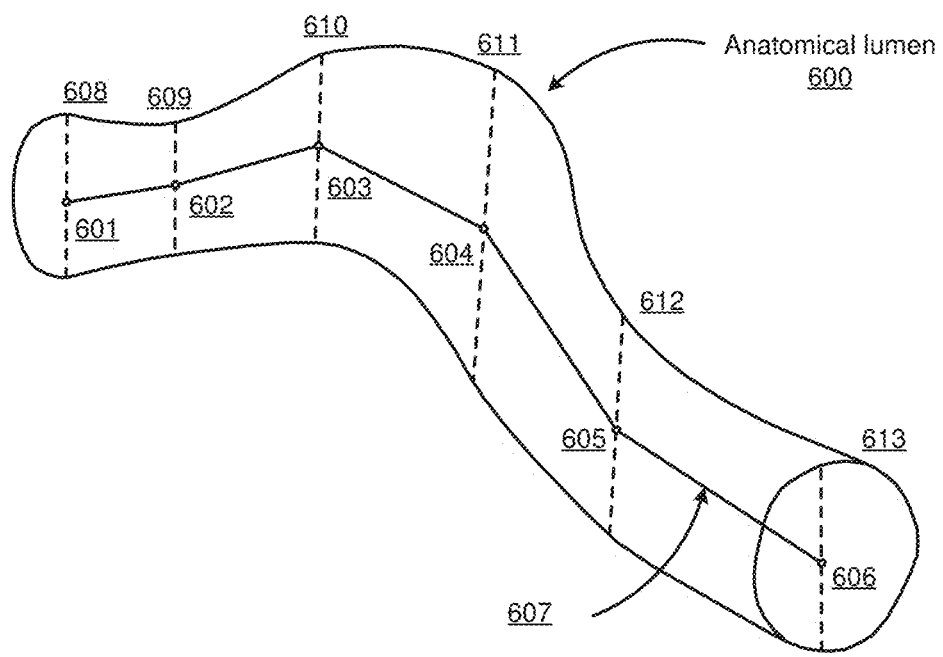
FIGS. 6A-6B show an example anatomical lumen and an example 3D model of the anatomical lumen, according to one embodiment.
Figure 6B:
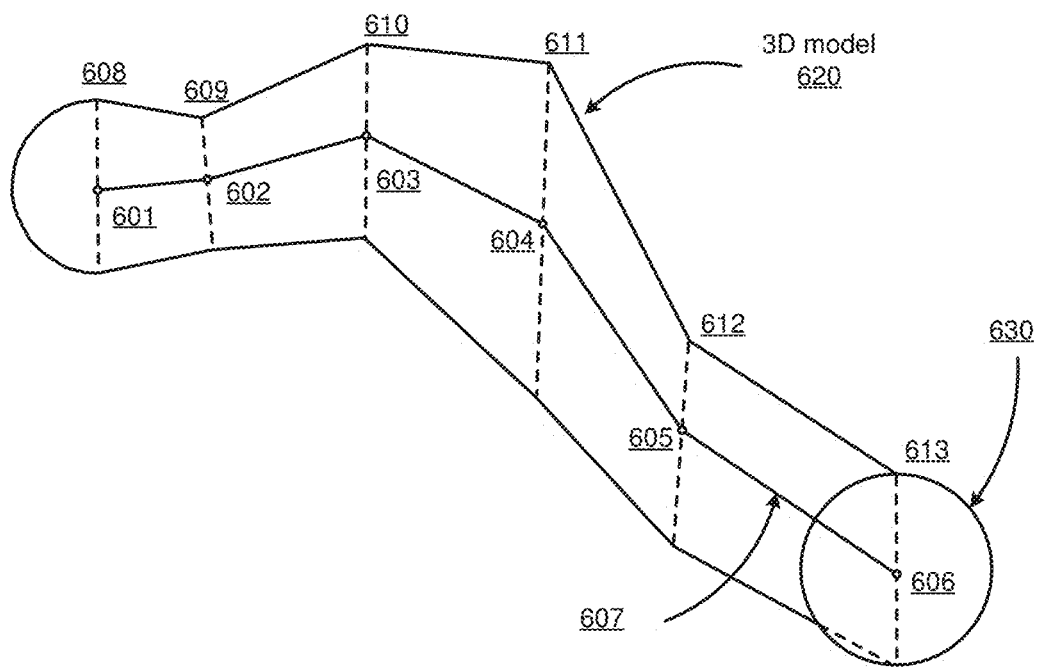

FIGS. 6A-6B show an example anatomical lumen 600 and an example 3D model 620 of the anatomical lumen, according to one embodiment. More specifically, FIGS. 6A-6B illustrate the relationships of centerline coordinates, diameter measurements and anatomical spaces between the actual anatomical lumen 600 and its 3D model 620. In FIG. 6A, the anatomical lumen 600 is roughly tracked longitudinally by centerline coordinates 601, 602, 603, 604, 605, and 606 where each centerline coordinate roughly approximates the center of the tomographic slice of the lumen. The centerline coordinates are connected and visualized by a centerline 607. The volume of the lumen can be further visualized by measuring the diameter of the lumen at each centerline coordinate, e.g., coordinates 608, 609, 610, 611, 612, and 613 represent the measurements of the lumen 600 corresponding to coordinates 601, 602, 603, 604, 605, and 606.

FIG. 6B shows the example 3D model 620 of the anatomical lumen 600 shown in FIG. 6A, according to one embodiment. In FIG. 6B, the anatomical lumen 600 is visualized in 3D space by first locating the centerline coordinates 601, 602, 603, 604, 605, and 606 in 3D space based on the centerline 607. As one example, at each centerline coordinate, the lumen diameter is visualized as a 2D circular space (e.g., the 2D circular space 630) with diameters 608, 609, 610, 611, 612, and 613. By connecting those 2D circular spaces to form a 3D space, the anatomical lumen 600 is approximated and visualized as the 3D model 620. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

In some embodiments, a pre-operative software package is also used to analyze and derive a navigation path based on the generated 3D model of the anatomical space. For example, the software package may derive a shortest navigation path to a single lesion (marked by a centerline coordinate) or to several lesions. This navigation path may be presented to the operator intra-operatively either in two-dimensions or three-dimensions depending on the operator's preference. In certain implementations, the navigation path (or at a portion thereof) may be pre-operatively selected by the operator. The path selection may include identification of one or more target locations (also simply referred to as a "target") within the patient's anatomy.

Figure 7:
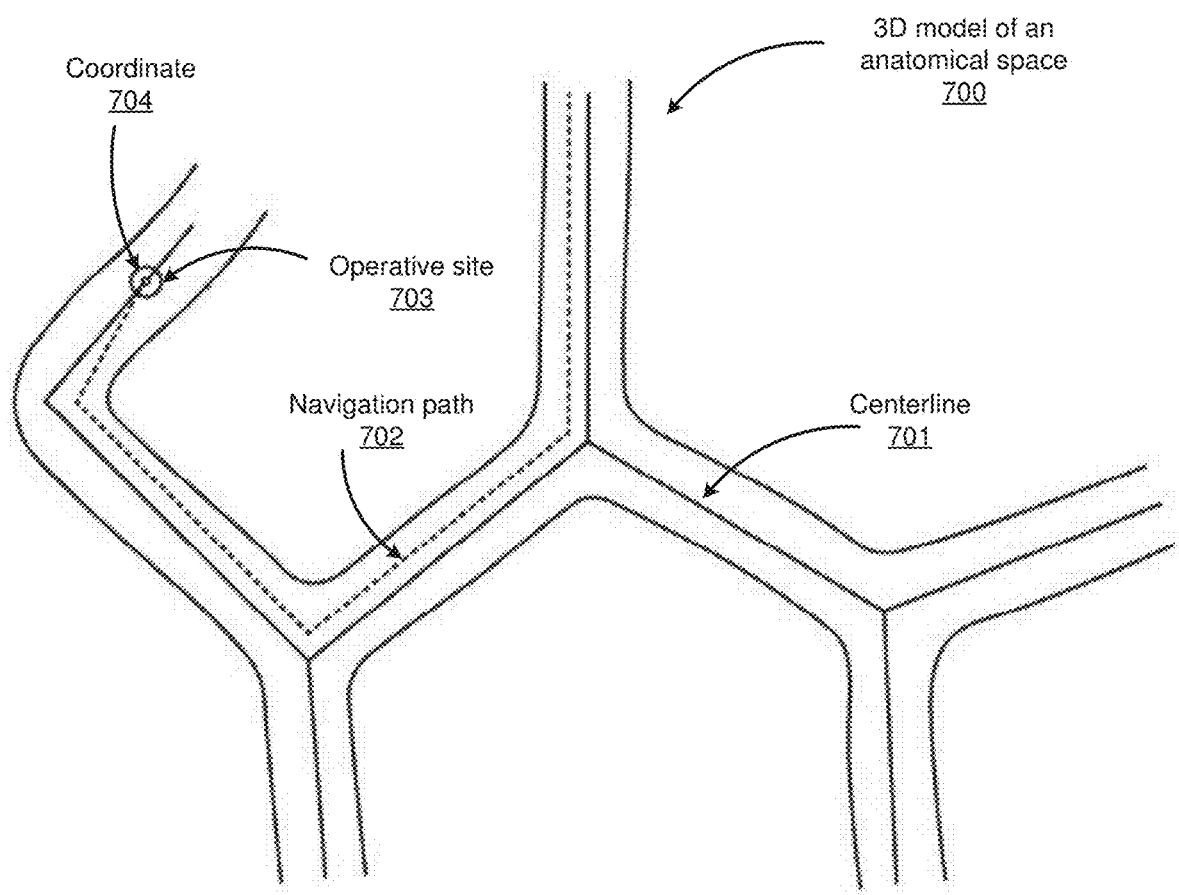
FIG. 7 shows a computer-generated 3D model representing an anatomical space, according to one embodiment.

FIG. 7 shows a computer-generated 3D model 700 representing an anatomical space, according to one embodiment. As discussed above in FIGS. 6A-6B, the 3D model 700 may be generated using a centerline 701 that was obtained by reviewing CT scans that were generated preoperatively. In some embodiments, computer software may be able to map a navigation path 702 within the tubular network to access an operative site 703 (or other target) within the 3D model 700. In some embodiments, the operative site 703 may be linked to an individual centerline coordinate 704, which allows a computer algorithm to topologically search the centerline coordinates of the 3D model 700 for the optimum path 702 within the tubular network. In certain embodiments, the topological search for the path 702 may be constrained by certain operator selected parameters, such as the location of one or more targets, one or more waypoints, etc.

In some embodiments, the distal end of the endoscopic tool within the patient's anatomy is tracked, and the tracked location of the endoscopic tool within the patient's anatomy is mapped and placed within a computer model, which enhances the navigational capabilities of the tubular network. In order to track the distal working end of the endoscopic tool, i.e., location and orientation of the working end, a number of approaches may be employed, either individually or in combination.

In a sensor-based approach to localization, a sensor, such as an EM tracker, may be coupled to the distal working end of the endoscopic tool to provide a real-time indication of the progression of the endoscopic tool. In EM-based tracking, an EM tracker, embedded in the endoscopic tool, measures the variation in the electromagnetic field created by one or more EM transmitters. The transmitters (or field generators), may be placed close to the patient (e.g., as part of the surgical bed) to create a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the endoscopic tool, for instance in leader and sheath in order to calculate the individual positions of those components. Accordingly, based on readings from an artificially-generated EM field, the EM tracker may detect changes in field strength as it moves through the patient's anatomy.

V. C. On-the-Fly EM Registration

Figure 8A:
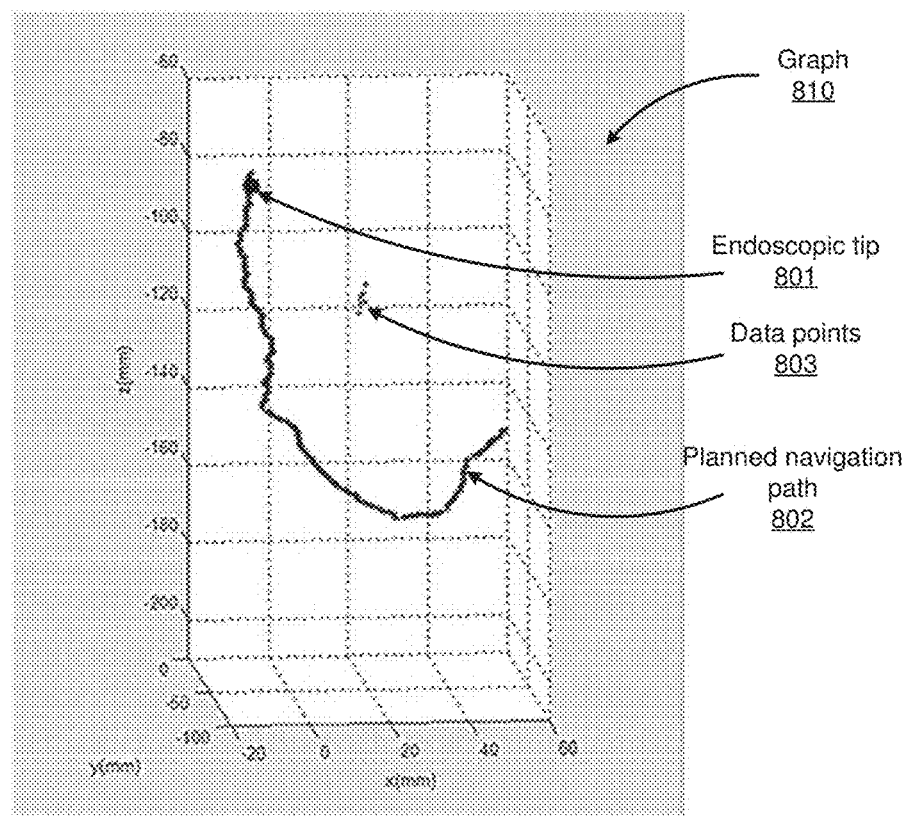
FIGS. 8A-8D show example graphs illustrating on-the-fly registration of an EM system to a 3D model of a path through a tubular network, according to one embodiment.

FIGS. 8A-8D show example graphs 810-840 illustrating on-the-fly registration of an EM system to a 3D model of a path through a tubular network, according to one embodiment. The navigation configuration system described herein allows for on-the-fly registration of the EM coordinates to the 3D model coordinates without the need for independent registration prior to an endoscopic procedure. In more detail, FIG. 8A shows that the coordinate systems of the EM tracking system and the 3D model are initially not registered to each other, and the graph 810 in FIG. 8A shows the registered (or expected) location of an endoscope tip 801 moving along a planned navigation path 802 through a branched tubular network (not shown here), and the registered location of the instrument tip 801 as well as the planned path 802 are derived from the 3D model. The actual position of the tip is repeatedly measured by the EM tracking system 505, resulting in multiple measured location data points 803 based on EM data. As shown in FIG. 8A, the data points 803 derived from EM tracking are initially located far from the registered location of the endoscope tip 801 expected from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from optical sensors (e.g., cameras) and robot data from robot commands. The 3D transformation between these points and collected EM data points will determine the initial registration of the EM coordinate system to the 3D model coordinate system.

Figure 8B:
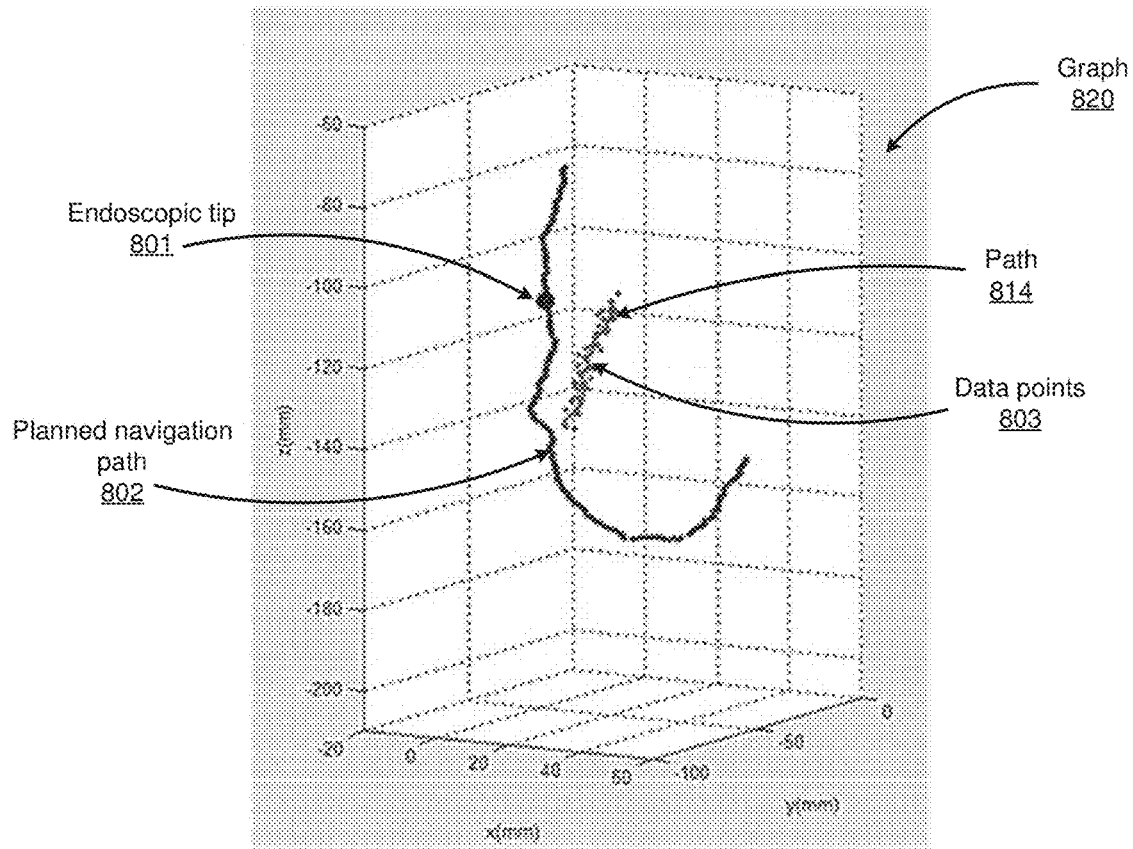

FIG. 8B shows a graph 820 at a later temporal stage compared with the graph 810, according to one embodiment. More specifically, the graph 820 shows the expected location of the endoscope tip 801 expected from the 3D model has been moved farther along the preplanned navigation path 802, as illustrated by the shift from the original expected position of the instrument tip 801 shown in FIG. 8A along the path to the position shown in FIG. 8B. During the EM tracking between generation of the graph 810 and generation of graph 820, additional data points 803 have been recorded by the EM tracking system but the registration has not yet been updated based on the newly collected EM data. As a result, the data points 803 in FIG. 8B are clustered along a visible path 814, but that path differs in location and orientation from the planned navigation path 802 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 8C:
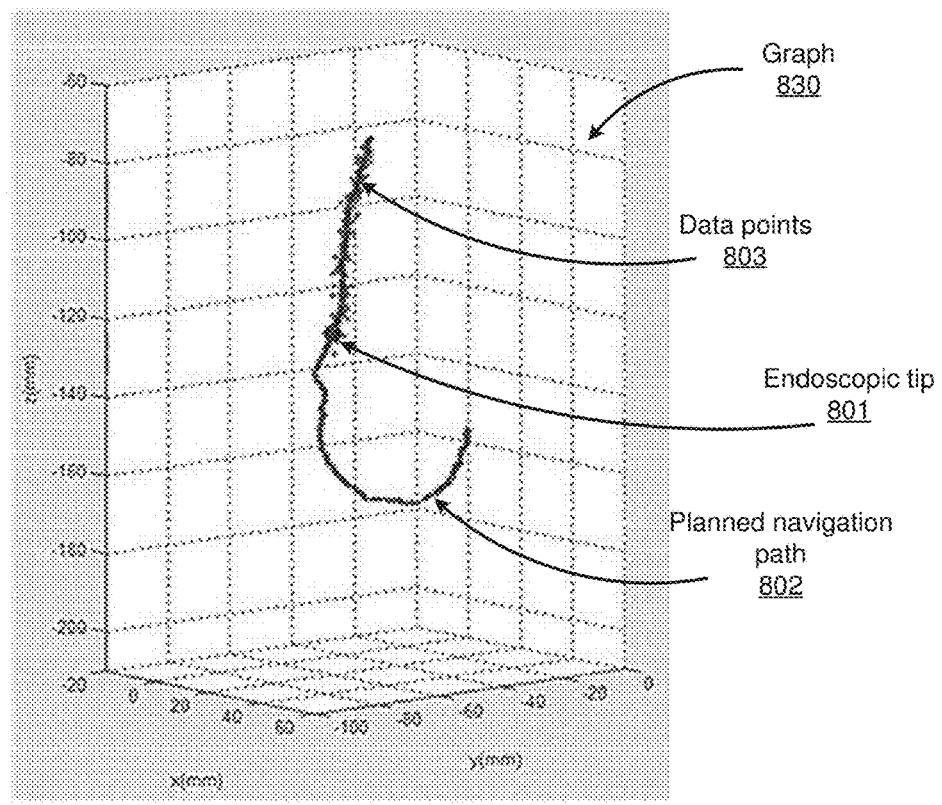

FIG. 8C shows a graph 830 shortly after the navigation configuration system has accumulated a sufficient amount of data to estimate the registration transform from EM to 3D model coordinates, according to one embodiment. The data points 803 in FIG. 8C have now shifted from their previous position as shown in FIG. 8B as a result of the registration transform. As shown in FIG. 8C, the data points 803 derived from EM data is now falling along the planned navigation path 802 derived from the 3D model, and each data point among the data points 803 is now reflecting a measurement of the expected position of endoscope tip 801 in the coordinate system of the 3D model. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

Figure 8D:
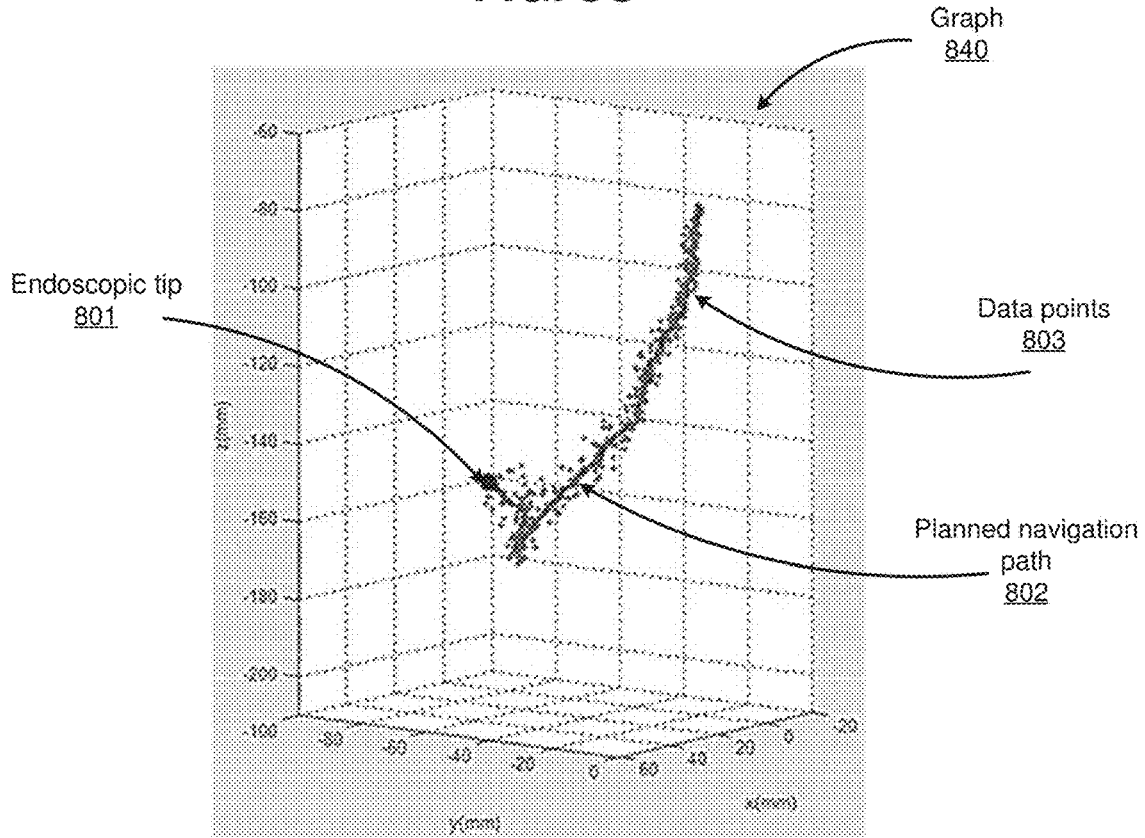

FIG. 8D shows an example graph 840 in which the expected location of the endoscope tip 801 has reached the end of the planned navigation path 802, arriving at the target location in the tubular network, according to one embodiment. As shown in FIG. 8D, the recorded EM data points 803 is now generally tracks along the planned navigation path 802, which represents the tracking of the endoscope tip throughout the procedure. Each data point reflects a transformed location due to the updated registration of the EM tracking system to the 3D model.

In some embodiments, each of the graphs shown in FIGS. 8A-8D can be shown sequentially on a display visible to a user as the endoscope tip is advanced in the tubular network. In some embodiments, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

Figure 8F:
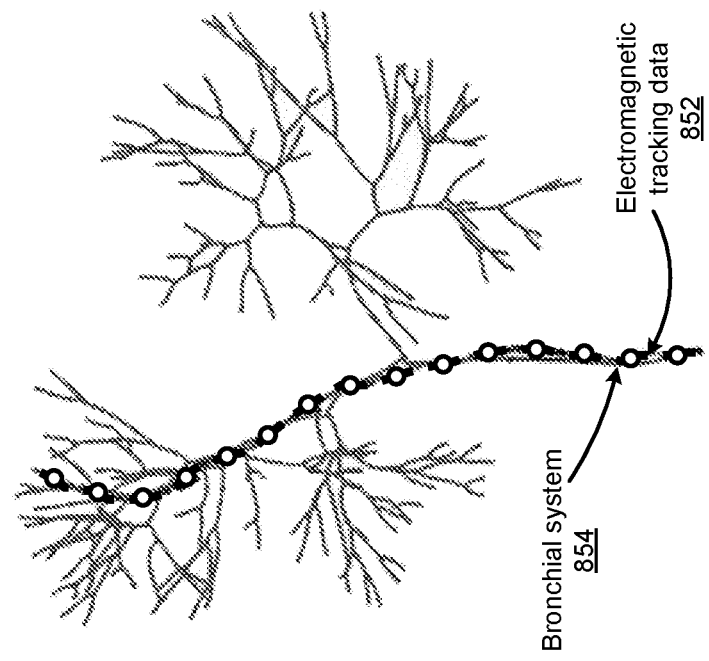
FIGS. 8E-8F show effect of an example registration of the EM system to a 3D model of a branched tubular network, according to one embodiment.
Figure 8E:
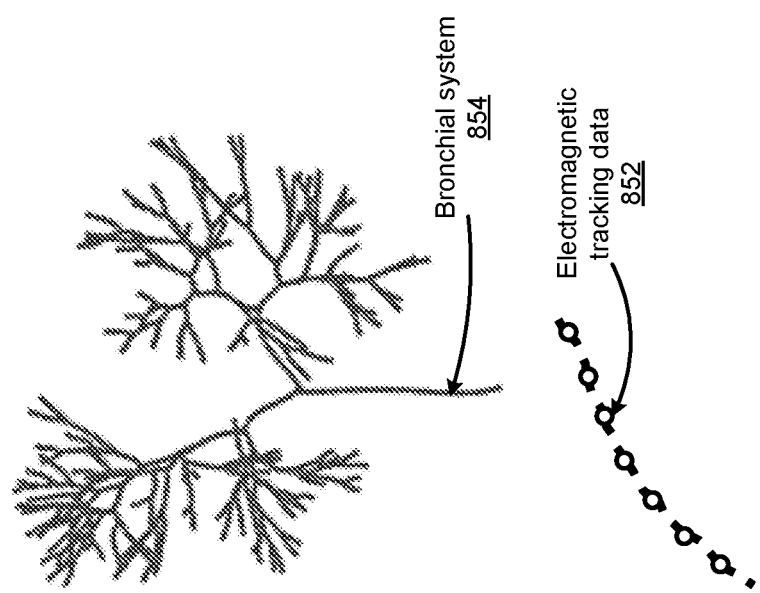

FIGS. 8E-8F show the effect of an example registration of the EM system to a 3D model of a branched tubular network, according to one embodiment. In FIGS. 8E-8F, 3D graphs showing electromagnetic tracking data 852 and a model of a patient's bronchial system 854 are illustrated without (shown in FIG. 8E) and with (shown in FIG. 8F) a registration transform. In FIG. 8E, without registration, tracking data 860 have a shape that corresponds to a path through the bronchial system 854, but that shape is subjected to an arbitrary offset and rotation. In FIG. 8F, by applying the registration, the tracking data 852 are shifted and rotated, so that they correspond to a path through the bronchial system 854.

VI. Navigation Configuration System

VI. A. High-Level Overview of Navigation Configuration System

Figure 9A:
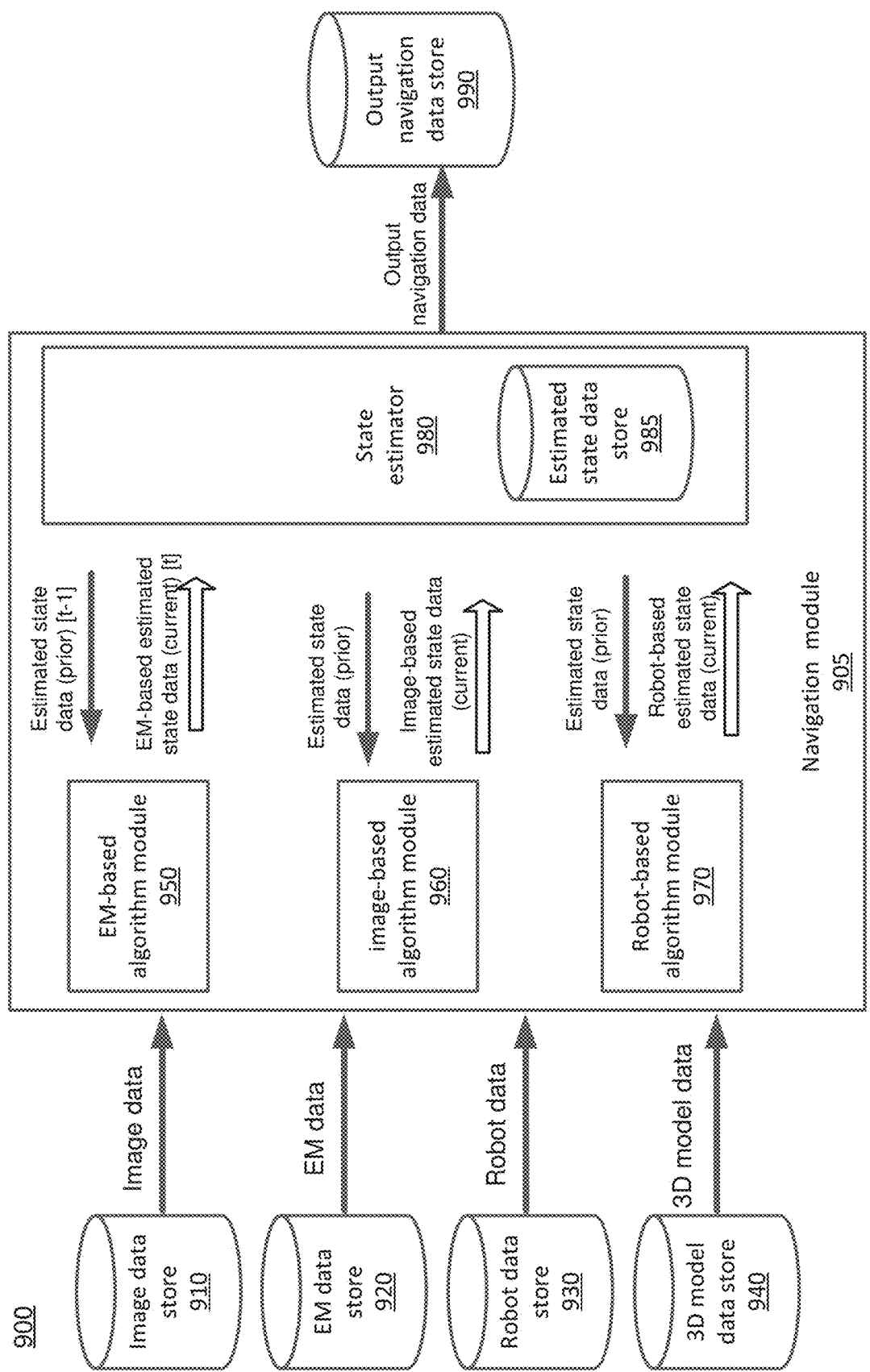
FIG. 9A shows a high-level overview of an example block diagram of a navigation configuration system, according to one embodiment.
Figure 9B:
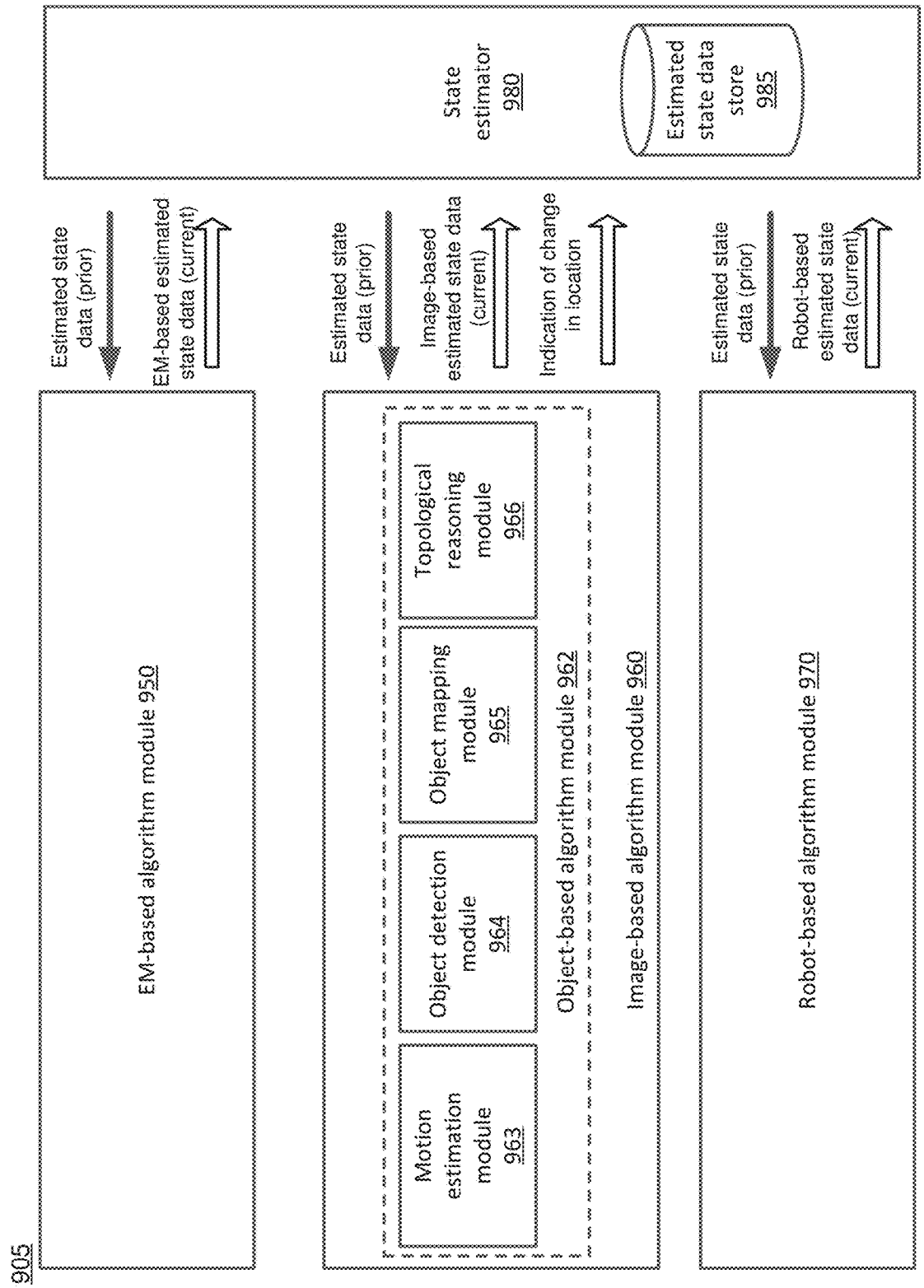
FIG. 9B shows an example block diagram of the navigation module shown in FIG. 9A, according to one embodiment.
Figure 9C:
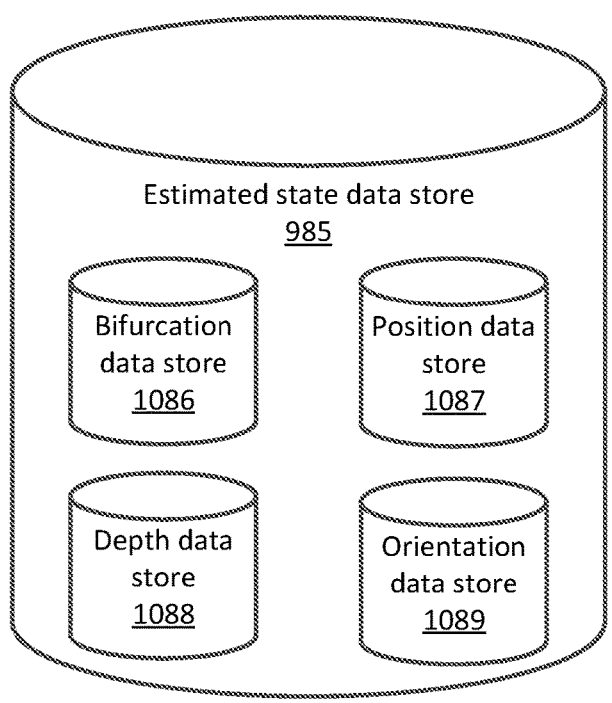
FIG. 9C shows example block diagram of the estimated state data store included in the state estimator, according to one embodiment.

FIGS. 9A-9C show example block diagrams of a navigation configuration system 900, according to one embodiment. More specifically, FIG. 9A shows a high-level overview of an example block diagram of the navigation configuration system 900, according to one embodiment. In FIG. 9A, the navigation configuration system 900 includes multiple input data stores, a navigation module 905 that receives various types of input data from the multiple input data stores, and an output navigation data store 990 that receives output navigation data from the navigation module. The block diagram of the navigation configuration system 900 shown in FIG. 9A is merely one example, and in alternative embodiments not shown, the navigation configuration system 900 can include different and/or addition entities. Likewise, functions performed by various entities of the system 900 may differ according to different embodiments. The navigation configuration system 900 may be similar to the navigational system described in U.S. Patent Publication No. 2017/0084027, published on Mar. 23, 2017, the entirety of which is incorporated herein by reference.

The input data, as used herein, refers to raw data gathered from and/or processed by input devices (e.g., command module, optical sensor, EM sensor, IDM) for generating estimated state information for the endoscope as well as output navigation data. The multiple input data stores 910-940 include an image data store 910, an EM data store 920, a robot data store 930, and a 3D model data store 940. Each type of the input data stores 910-940 stores the name-indicated type of data for access and use by a navigation module 905. Image data may include one or more image frames captured by the imaging device at the instrument tip, as well as information 911 such as frame rates or timestamps that allow a determination of the time elapsed between pairs of frames. Robot data may include data related to physical movement of the medical instrument or part of the medical instrument (e.g., the instrument tip or sheath) within the tubular network. Example robot data includes command data instructing the instrument tip to reach a specific anatomical site and/or change its orientation (e.g., with a specific pitch, roll, yaw, insertion, and retraction for one or both of a leader and a sheath) within the tubular network, insertion data representing insertion movement of the part of the medical instrument (e.g., the instrument tip or sheath), IDM data, and mechanical data representing mechanical movement of an elongate member of the medical instrument, for example motion of one or more pull wires, tendons or shafts of the endoscope that drive the actual movement of the medial instrument within the tubular network. EM data may be collected by EM sensors and/or the EM tracking system as described above. 3D model data may be derived from 2D CT scans as described above.

The output navigation data store 990 receives and stores output navigation data provided by the navigation module 905. Output navigation data indicates information to assist in directing the medical instrument through the tubular network to arrive at a particular destination within the tubular network, and is based on estimated state information for the medical instrument at each instant time, the estimated state information including the location and orientation of the medical instrument within the tubular network. In one embodiment, as the medical instrument moves inside the tubular network, the output navigation data indicating updates of movement and location/orientation information of the medical instrument is provided in real time, which better assists its navigation through the tubular network.

To determine the output navigation data, the navigation module 905 locates (or determines) the estimated state of the medical instrument within a tubular network. As shown in FIG. 9A, the navigation module 905 further includes various algorithm modules, such as an EM-based algorithm module 950, an image-based algorithm module 960, and a robot-based algorithm module 970, that each may consume mainly certain types of input data and contribute a different type of data to a state estimator 980. As illustrated in FIG. 9A, the different kinds of data output by these modules, labeled EM-based data, the image-based data, and the robot-based data, may be generally referred to as "intermediate data" for sake of explanation. The detailed composition of each algorithm module and of the state estimator 980 is more fully described below.

VI. B. Navigation Module

FIG. 9B shows an example block diagram of the navigation module 905 shown in FIG. 9A, according to one embodiment. As introduced above, the navigation module 905 further includes a state estimator 980 as well as multiple algorithm modules that employ different algorithms for navigating through a tubular network. For clarity of description, the state estimator 980 is described first, followed by the description of the various modules that exchange data with the state estimator 980.

VI. B. 1 State Estimator

The state estimator 980 included in the navigation module 905 receives various intermediate data and provides the estimated state of the instrument tip as a function of time, where the estimated state indicates the estimated location and orientation information of the instrument tip within the tubular network. The estimated state data are stored in the estimated data store 985 that is included in the state estimator 980.

FIG. 9C shows an example block diagram of the estimated state data store 985 included in the state estimator 980, according to one embodiment. The estimated state data store 985 may include a bifurcation data store 1086, a position data store 1087, a depth data store 1088, and an orientation data store 1089, however this particular breakdown of data storage is merely one example, and in alternative embodiments not shown, different and/or additional data stores can be included in the estimated state data store 985.

The various stores introduced above represent estimated state data in a variety of ways. Specifically, bifurcation data refers to the location of the medical instrument with respect to the set of branches (e.g., bifurcation, trifurcation or a division into more than three branches) within the tubular network. For example, the bifurcation data can be set of branch choices elected by the instrument as it traverses through the tubular network, based on a larger set of available branches as provided, for example, by the 3D model which maps the entirety of the tubular network. The bifurcation data can further include information in front of the location of the instrument tip, such as branches (bifurcations) that the instrument tip is near but has not yet traversed through, but which may have been detected, for example, based on the tip's current position information relative to the 3D model, or based on images captured of the upcoming bifurcations.

Position data indicates three-dimensional position of some part of the medical instrument within the tubular network or some part of the tubular network itself. Position data can be in the form of absolute locations or relative locations relative to, for example, the 3D model of the tubular network. As one example, position data can include an indication of the position of the location of the instrument being within a specific branch. The identification of the specific branch may also be stored as a segment identification (ID) which uniquely identifies the specific segment of the model in which the instrument tip is located.

Depth data indicates depth information of the instrument tip within the tubular network. Example depth data includes the total insertion (absolute) depth of the medical instrument into the patient as well as the (relative) depth within an identified branch (e.g., the segment identified by the position data store 1087). Depth data may be determined based on position data regarding both the tubular network and medical instrument.

Orientation data indicates orientation information of the instrument tip, and may include overall roll, pitch, and yaw in relation to the 3D model as well as pitch, roll, raw within an identified branch.

Turning back to FIG. 9B, the state estimator 980 provides the estimated state data back to the algorithm modules for generating more accurate intermediate data, which the state estimator uses to generate improved and/or updated estimated states, and so on forming a feedback loop. For example, as shown in FIG. 9B, the EM-based algorithm module 950 receives prior EM-based estimated state data, also referred to as data associated with timestamp "t−1." The state estimator 980 uses this data to generate "estimated state data (prior)" that is associated with timestamp "t−1." The state estimator 980 then provides the data back to the EM-based algorithm module. The "estimated state data (prior)" may be based on a combination of different types of intermediate data (e.g., robotic data, image data) that is associated with timestamp "t−1" as generated and received from different algorithm modules. Next, the EM-based algorithm module 950 runs its algorithms using the estimated state data (prior) to output to the state estimator 980 improved and updated EM-based estimated state data, which is represented by "EM-based estimated state data (current)" here and associated with timestamp t. This process continues to repeat for future timestamps as well.

As the state estimator 980 may use several different kinds of intermediate data to arrive at its estimates of the state of the medical instrument within the tubular network, the state estimator 980 is configured to account for the various different kinds of errors and uncertainty in both measurement and analysis that each type of underlying data (robotic, EM, image) and each type of algorithm module might create or carry through into the intermediate data used for consideration in determining the estimated state. To address these, two concepts are discussed, that of a probability distribution and that of confidence value.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the tubular network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution. Different methods or modalities can be used to generate the probabilities, which will vary by algorithm module as more fully described below with reference to later figures.

In contrast, the "confidence value," as used herein, reflects a measure of confidence in the estimation of the state provided by one of the algorithms based one or more factors. For the EM-based algorithms, factors such as distortion to EM Field, inaccuracy in EM registration, shift or movement of the patient, and respiration of the patient may affect the confidence in estimation of the state. Particularly, the confidence value in estimation of the state provided by the EM-based algorithms may depend on the particular respiration cycle of the patient, movement of the patient or the EM field generators, and the location within the anatomy where the instrument tip locates. For the image-based algorithms, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM} * P_{1,EM} + C_{Image} * P_{1,Image} + C_{Robot} * P_{1,Robot};$$

$$S_2 = C_{EM} * P_{2,EM} + C_{Image} * P_{2,Image} + C_{Robot} * P_{2,Robot};$$

$$S_3 = C_{EM} * P_{3,EM} + C_{Image} * P_{3,Image} + C_{Robot} * P_{3,Robot}.$$

In the example mathematical equation above, $S_i (i=1, 2, 3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represents the probabilities for segment i.

To better illustrate the concepts of probability distributions and confidence value associated with estimate states, a detailed example is provided here. In this example, a user is trying to identify segment where an instrument tip is located in a certain trifurcation within a central airway (the predicted region) of the tubular network, and three algorithms modules are used including EM-based algorithm, image-based algorithm, and robot-based algorithm. In this example, a probability distribution corresponding to the EM-based algorithm may be 20% in the first branch, 30% in the second branch, and 50% in the third (last) branch, and the confidence value applied to this EM-based algorithm and the central airway is 80%. For the same example, a probability distribution corresponding to the image-based algorithm may be 40%, 20%, 40% for the first, second, and third branch, and the confidence value applied to this image-based algorithm is 30%; while a probability distribution corresponding to the robot-based algorithm may be 10%, 60%, 30% for the first, second, and third branch, and the confidence value applied to this image-based algorithm is 20%. The difference of confidence values applied to the EM-based algorithm and the image-based algorithm indicates that the EM-based algorithm may be a better choice for segment identification in the central airway, compared with the image-based algorithm. An example mathematical calculation of a final estimated state can be:

for the first branch: 20%*80%+40%*30%+10%*20%=30%; for the second branch: 30%*80%+20%*30%+60%*20%=42%; and for the third branch: 50%*80%+40%*30%+30%*20%=58%.

In this example, the output estimated state for the instrument tip can be the result values (e.g., the resulting 30%, 42% and 58%), or derivative value from these result values such as the determination that the instrument tip is in the third branch.

As above the estimated state may be represented in a number of different ways. For example, the estimated state may further include an absolute depth from airway to location of the tip of the instrument, as well as a set of data representing the set of branches traversed by the instrument within the tubular network, the set being a subset of the entire set of branches provided by the 3D model of the patient's lungs, for example. The application of probability distribution and confidence value on estimated states allows improved accuracy of estimation of location and/or orientation of the instrument tip within the tubular network.

VI. B. 2 Algorithm Modules

As shown in FIG. 9B, the algorithm modules include an EM-based algorithm module 950, an image-based algorithm module 960, and a robot-based algorithm module 970. The algorithm modules shown in FIG. 9B is merely one example, and in alternative embodiments, different and/or additional algorithm modules involving different and/or additional navigation algorithms can also be included in the navigation module 905.

VI. B. 2. i. Image-Based Algorithm Module

Turning back to FIG. 9B, the image-based algorithm module 960 uses image data to determine the estimated state of the instrument within the tubular network. The image-based algorithm module 960 further includes one or more different types of image-based algorithm modules that employ different image-based algorithms. As shown in FIG. 9B, one example including an object-based algorithm module 962 is shown. In alternative embodiments not shown, other types of image-based algorithms may be employed and corresponding algorithm modules may be included in the image-based algorithm module 960. In addition to determining the estimated state of the instrument, the image-based algorithm module 960 may also detect a change of location of the instrument within the luminal network caused by movement of the luminal network relative to the instrument and provide an indication of the detected change in location to the state estimator 980. Further detail regarding aspects of the detection of the change in location of the instrument will be provided below in connection with FIG. 11.

The object-based algorithm module 962 detects and analyzes objects present in the field of view of the image data, such as branch openings or particles, to determine estimated state. In one embodiment, it includes an object detection module 963, and object mapping module 964, a topological reasoning module 965, and a motion estimation module 966. In some embodiments, it may or may not be necessary to apply the different modules 963, 964, 965 and 966 in a fixed sequential order, and when actually executing a process of object-based algorithm described by the object-based algorithm module 962, the order of employing each module within the module 962 is a different order than shown in FIG. 9B.

Figure 10A:
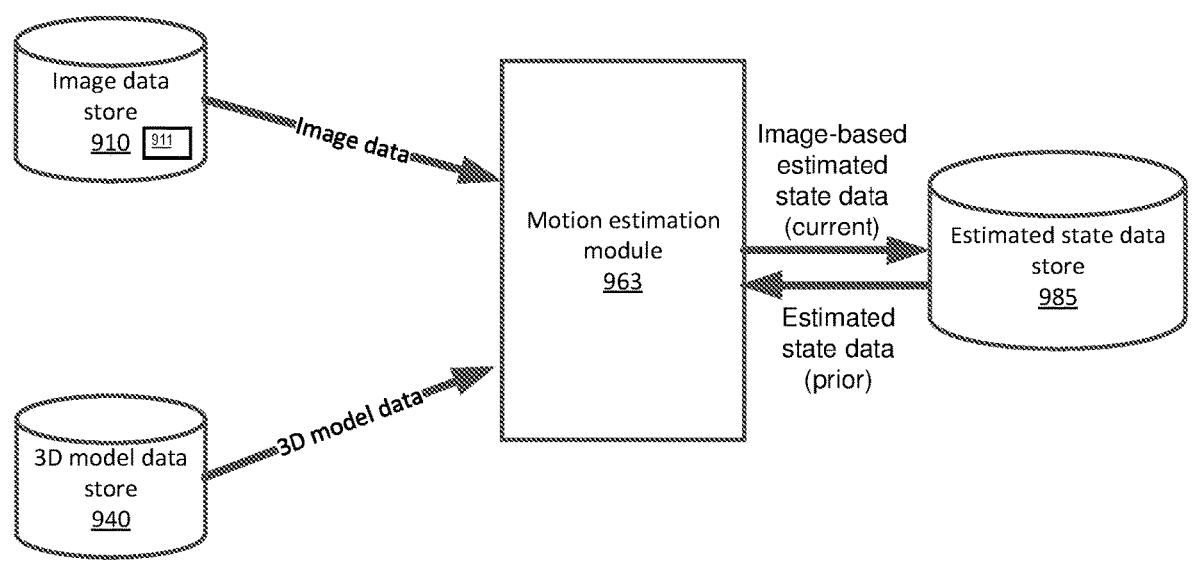
FIG. 10A shows an example block diagram of the motion estimation module in accordance with aspects of this disclosure.

Turning to FIG. 10A, the motion estimation module 963 receives as inputs image data from the image data store 910, estimated state data (prior) (specifically bifurcation data), from the estimated state data store 985 as well as the 3D model data from the 3D model data store 940. Based on the received image data, the motion estimation module 963 measures a movement of the medical instrument between multiple image frames based on the received image data. Example techniques used include optical flow and image registration techniques, among others. This measurement determines a differential movement, such as forward-backward motion or roll motion, of the instrument tip in its own local frame of reference. This movement can be combined with the prior estimated state input to calculate a new estimated state. In particular, a forward (or backward) movement can translate into an increase (or decrease) in depth relative to a prior estimated state. Similarly, a differential roll translates into a change in roll angle relative to a prior estimated state. These measurements allow an estimation of movement through the tubular network. As above, these estimations may be represented as a probability distribution (e.g., a roll angle of the medical instrument of 40±5 degrees represented by a Gaussian distribution). The output estimated state is stored in the estimated state data store 985.

In one embodiment, in a case where the estimated state and bifurcation data for a particular instant in time indicate that the instrument tip is at or near a branch point, this movement measurement may include an identification of an estimated new branch that the instrument tip is estimated to be entering or have entered. For example, if the bifurcation data indicates that the endoscope tip is at a branch point, pitch and yaw movements can be measured to determine changes in pointing angle, and the new estimated angle can be compared with the expected angles of different branches in the 3D model of the tubular network. A determination can then be made of which branch the endoscope is facing towards when it is moved into a new branch. Estimated state data reflecting each of these estimates of new position, orientation, and/or branch entry are output to the state estimator 980.

Figure 10B:
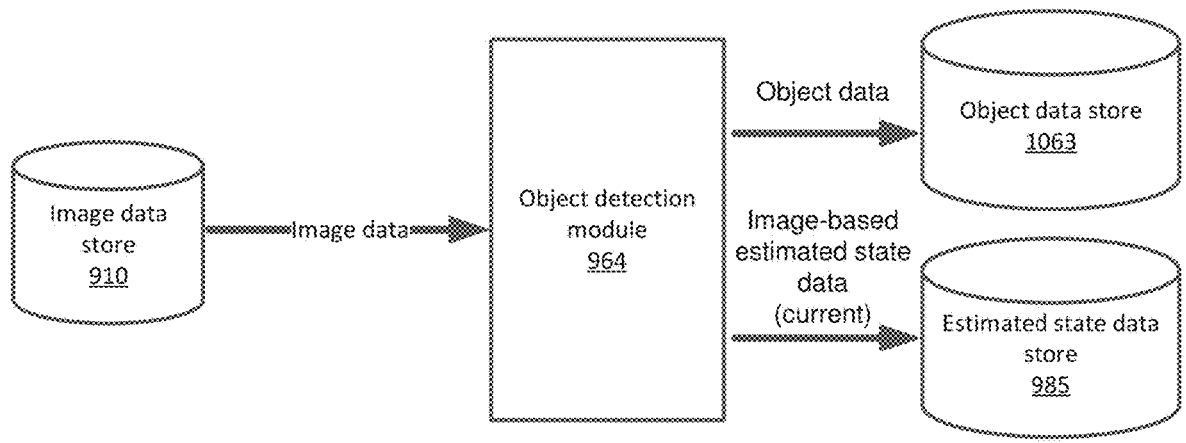
FIG. 10B shows an example block diagram of the object detection module, according to one example.

FIG. 10B shows an example block diagram of the object detection module 964, according to one example. The object detection module 964 receives as inputs image data (e.g., image frames), and outputs object data to an object data store 1063 as well as estimated state data to the estimated state data store 985. Object data indicates information about what objects were identified, as well as positions, orientations, and sizes of objects represented as probabilities.

Specifically, the object detection module 964 detects, within an image, one or more objects and one or more points of interest of the object(s) that may indicate branch points in a tubular network, and then determines their position, size, and orientation. The objects detected by the object detection module 964 may also be referred to as "points of interest," which may include, for example, one or more identifiable pixels within an image. In certain embodiments, the points of interest may comprise a set of one or more pixels which can be detected over a sequence of one or more images. In some implementations, the detected object may comprise one of more points of interest (e.g., image features) detected using image processing techniques of the related art, such as speeded up robust features (SURF) and scale-invariant feature transform (SIFT). However, any technique which can reliably detect and track one or more pixels through a series of images can be used to detect the points of interest which can be used in the image processing techniques described herein.

In certain implementations, objects may be calculated or represented in the object detection module 964 as being two-dimensional shapes, such as circles/ovals/ellipses for detected branch points. This corresponds to the fact that the image data used to capture the objects are images from the camera on the instrument tip pointed usually along an axis substantially parallel to the direction of the segment in which the instrument is located. As a consequence, objects such as branches in the tubular network appear as simple shapes such as ellipses in the images. In one embodiment, in a given image within a tubular network, each branch will typically appear as a dark, approximately elliptical region, and these regions may be detected automatically by a processor, using region-detection algorithms such as maximally stable extremal regions (MSER) as objects. These regions may then be fit to define an object (e.g., ellipse), with appropriate free parameters such as ellipse center, major and minor axes, and angle within the image. The roll measurement and the identified matching between model lumens and lumens in the image are also output to the state estimator 980, as well as topological reasoning module 966. An example of identified objects superimposed on an image of a bronchial network, along with a link joining their centers, is described with reference to FIGS. 11A-11B.

In one embodiment, an "airway" can also be identified as an object present in the image data. The object detection module 964 may use light reflective intensity combined with other techniques to identify airways.

The object detection module 964 may further track detected objects or points of interest across a set of sequential image frames. The object tracking may be used to detect which branch has been entered from among a set of possible branches in the tubular network. Alternatively or in addition, the tracking of objects may be used to detect a change of location of the instrument within the luminal network caused by movement of the luminal network relative to the instrument as described in greater detail below. Tracking the relative positions of the objects within the image frames may also be used to determine a local, absolute measurement of roll angle within a branched network.

Figure 10C:
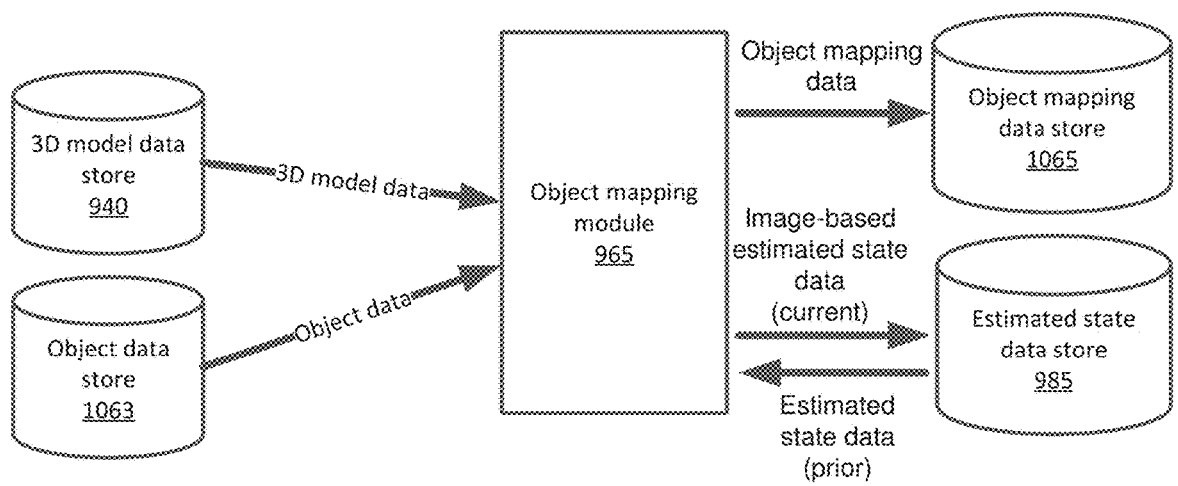
FIG. 10C shows an example block diagram of the object mapping module, according to one embodiment.

FIG. 10C shows an example block diagram of the object mapping module 965, according to one embodiment. The object mapping module 965 receives as inputs 3D model data from the 3D model data store 940, object data (e.g., detected objects such as shapes representing possible branches in the tubular network) from the object data store 1063, and estimated state data (prior) from the estimated state data store 985.

Based on the received input data, the object mapping module 965 outputs object mapping data to an object mapping data store 1065 as well as image-based estimated state data (current) to the estimated state data store 985. As one example, the object mapping data indicates mapping information between physical branches (lumens) shown in image data (based on the detected objects) and virtual branch information generated by 3D model. The estimated state data (current) generated by module 965 includes identification of each branch of the tubular network visible within the image as well as an estimate of the roll of the endoscope tip relative to the 3D model. As above, the estimated state data (current) can be represented as a probability distribution. The identification of the visible lumens may include coordinates in x and y of each identified lumen center within the image, for example based on object sizes correlated with the 3D model virtual image data, as well as an association of each identified lumen location with a particular branch of the tubular network.

In some embodiments, since the 3D model is generated prior to the endoscopic procedure, the virtual images of the tubular network may be pre-computed to speed up processing. In alternative embodiments not shown, the tubular network may be represented by a structure such as a tree diagram of lumen midlines, with each such midline describing a 3D path, so that an expected position of local branch centers as seen from any arbitrary perspective may be compared to the identified actual locations of branch centers based on EM data and/or robot data.

Figure 11A:
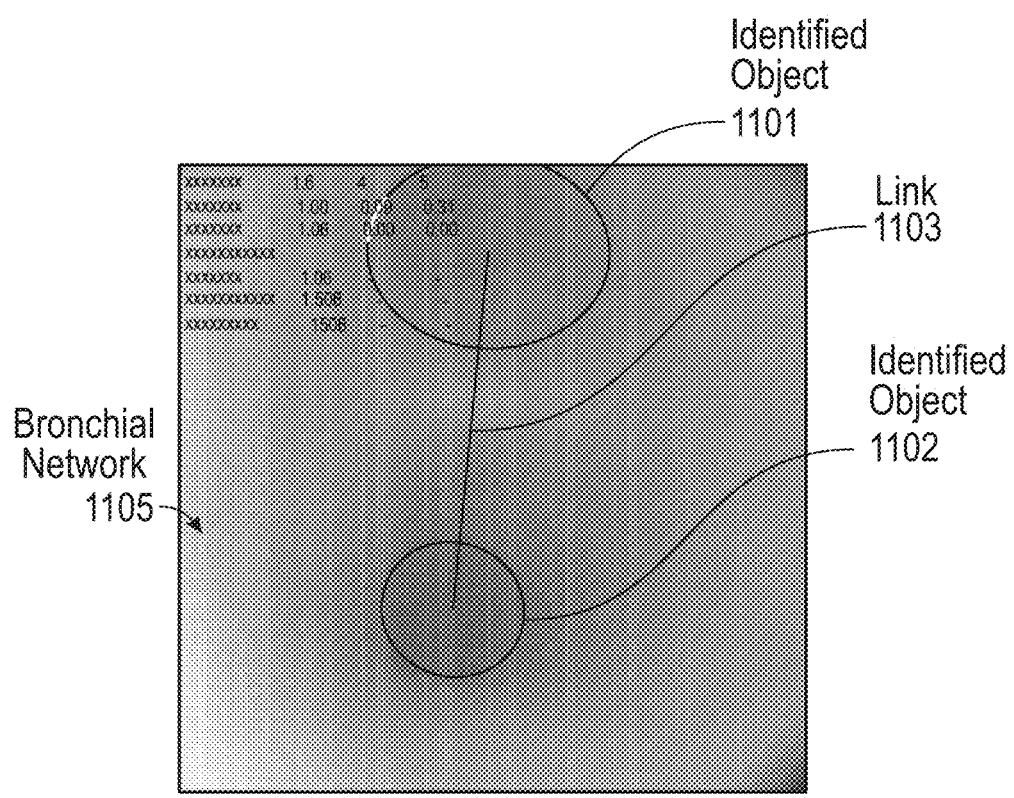
FIGS. 11A-11B, show an example object-to-lumen mapping performed by the object mapping module, according to one embodiment.
Figure 11B:
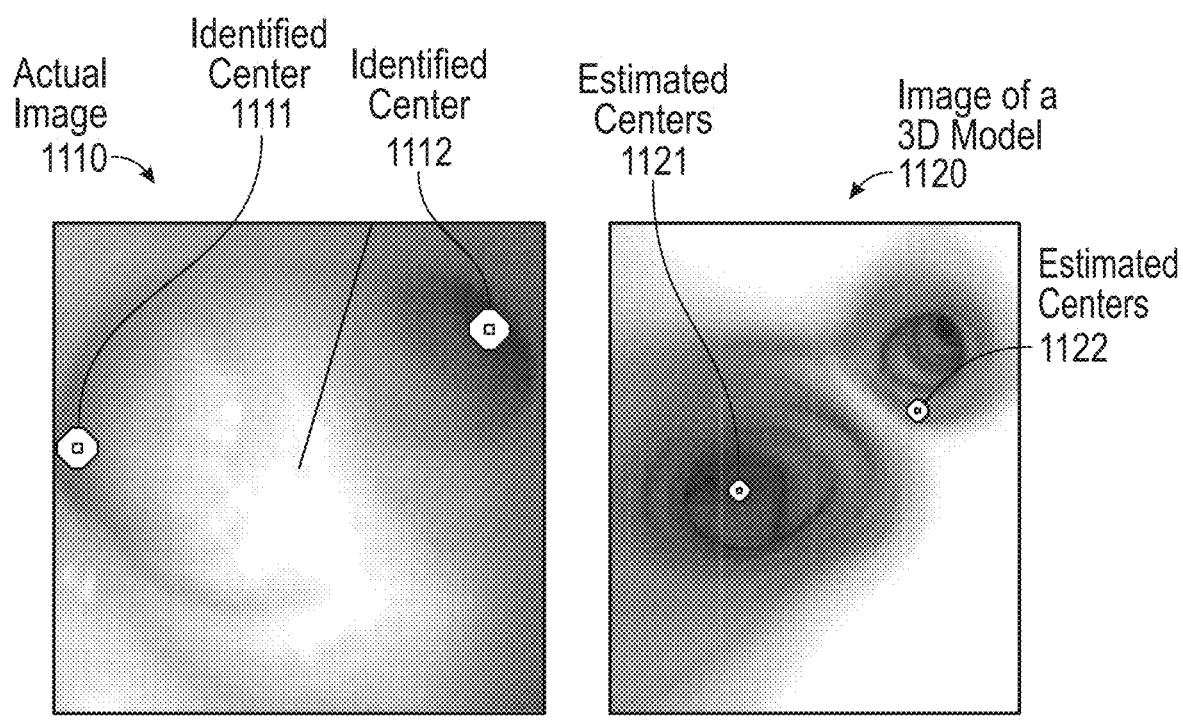

FIGS. 11A-11B, show an example object-to-lumen mapping performed by the object mapping module 965, according to one embodiment. More specifically, FIG. 11A shows two example identified objects 1101 and 1102 superimposed on an image of a bronchial network 1105 along with a link 1103 connecting centers of the two objects, according to one embodiment. In the illustrated example, the identified objects 1101 and 1102 are ellipse-shaped.

FIG. 11B shows a matching between airway lumens in an actual image 1110 of a real bronchial network and a corresponding virtual image 1120 from a 3D model of that same network, according to one embodiment. In the actual image 1110, ellipses are identified corresponding to two different branches, located with identified centers 1111 and 1112, which, in one embodiment, indicates centerline coordinates of the branches as described above in FIGS. 6A-6B. The 3D model virtual image 1120 is a simulated representation of the real bronchial network shown in the actual image 1110, and the estimated centers 1121 and 1122 of the endoscope tip as determined by the state estimator 980 are shown corresponding to the positions of the identified centers 1111 and 1112.

If both images 1110 and 1120 are presented to a user via a user interface, the 3D model image 1120 may be rotated or translated to increase the closeness of fit between actual image 1110 and virtual image 1120, and the amount of roll needed for the rotation or translation can be output as a correction to the current estimated state (e.g., roll of the instrument tip).

In one embodiment, the probability applied to a possible estimated state as generated by the object mapping module 965 is based on the closeness of fit between the identified centers 1111 and 1112 detected in the actual image 1110 and estimated centers 1121 and 1121 in the 3D model image 1120, and as one example, the probability of being in the lumen with identified center 1112 drops as the distance between the estimated center 1122 and identified center 1112 increases.

Figure 10D:
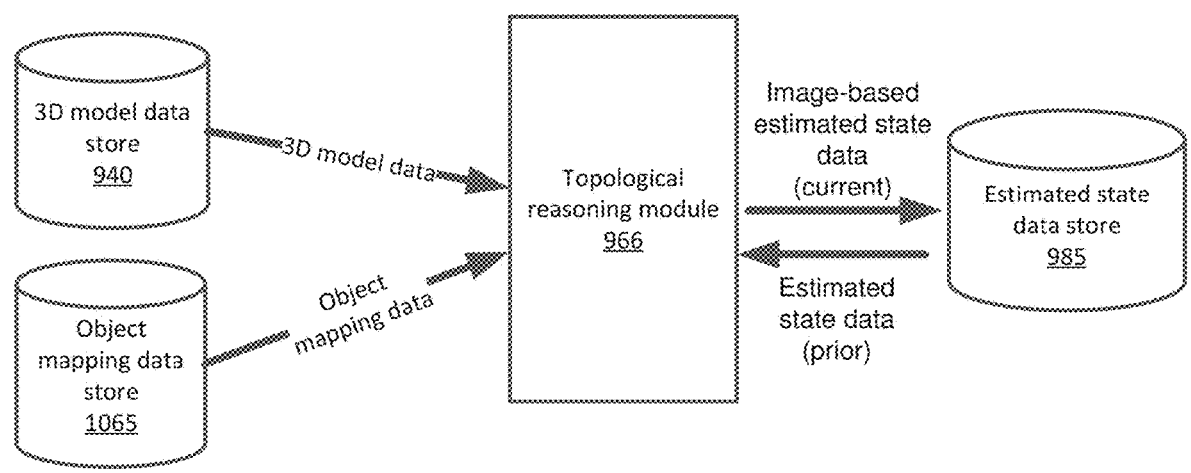
FIG. 10D shows an example block diagram of the topological reasoning module, according to one embodiment.

FIG. 10D shows an example block diagram of the topological reasoning module 966, according to one embodiment. The topological reasoning module 966 receives as input image data from the 3D model data from the 3D model data store 940, object mapping data from the object mapping data store 1065, and estimated state data (prior) from the estimated state data store 985.

Based on the received data, the topological reasoning module 966 determines which branch the endoscope tip is facing towards, thereby generating a prediction of which branch will be entered if the endoscope is moved forward. As above, the determination may be represented as a probability distribution. In one embodiment, when the instrument tip is moving forward, the topological reasoning module 966 determines that a new branch of the tubular network has been entered and identifies which branch the tip has moved into. The determination of which branch is being faced and which segment is entered may be made, for example, by comparing the relative sizes and locations of different identified objects (e.g., ellipses). As one example, as a particular lumen branch is entered, a corresponding detected object will grow larger in successive image frames, and will also become more centered in those frames. If this is behavior is identified for one of the objects, the topological reasoning module 966 assigns an increasingly large probability to a corresponding estimated state as the endoscope tip moves towards the lumen associated with that object. Other branches are assigned correspondingly lower probabilities, until finally their object shapes disappear from images entirely. In one embodiment, the probability of the medical instrument being in those branches depends only on the probability that the branches were misidentified by the object mapping module 964. The output of the topological reasoning module 966 is image-based estimated state data representing estimated probabilities of being in each of a set of possible branches within the branched network.

VII. Image-Based Detection of Physiological Noise

Pulmonologists can prevent intra-operative trauma by basing their decisions and actions on the respiratory cycle of the patient. One example of such an action is insertion of a biopsy tool to collect tissue samples, for example via bronchoscopy. At or near the periphery of the lung the airways may be narrow, and the circumference of the airways changes depending on the respiratory phase of the lung. The diameter of an airway expands as a patient inhales in the inspiration phase of the respiratory cycles and constricts as the patient exhales during the expiration phase of the cycle. During a procedure, a pulmonologist can observe the patient to determine whether they are in the inspiration phase or the expiration phase in order to decide whether a particular tool or endoscope of fixed diameter can enter the airway. An airway can close around a tool during expiration without causing trauma, however forcing a tool through a constricted airway during the expiration phase can cause critical trauma, for example by puncturing a blood vessel.

The aforementioned problems, among others, are addressed in certain embodiments by the luminal network navigation systems and techniques described herein. Some embodiments of the disclosed luminal network navigation systems and techniques relate to incorporating respiratory frequency and/or magnitude into a navigation framework to implement patient safety measures (e.g., instrument control techniques, user interface alerts, notifications, and the like).

A patient's respiratory cycle may also affect the accuracy of the detection of the position and/or orientation of an instrument inserted into the patient's airways. Thus, some embodiments of the disclosed bronchoscopy navigation systems and techniques relate to identifying, and/or compensating for, motion caused by patient respiration in order to provide a more accurate identification of the position of an instrument within patient airways. For example, an instrument positioned within patient airways can be provided with an EM sensor. The navigation system can filter instrument position information from the EM sensor to remove signal noise due to cyclic motion of the respiratory passages caused by respiration. A frequency of the cyclic respiratory motion can be obtained from data from one or more additional sensors. In some implementations, inspiration and expiration cycles can be determined based on data from additional EM sensor(s), accelerometer(s), and/or acoustic respiratory sensor(s) placed on the body of the patient in one example. In some implementations, the frequency can be obtained from other types of sensors or systems, for example respiratory cycle information from a ventilator used to control patient breathing, or respiratory cycle information extracted from automated analysis of images received from an optical sensor positioned to observe the patient.

Under certain circumstances, the filtering of the patient's respiration from the position information received from the EM sensor may not be sufficient to determine a sufficiently accurate estimate of the position of the instrument. For example, when additional EM sensor(s) are placed on the exterior of a patient's body, the EM sensors may detect the motion due to respiration in a transverse direction. That is, the EM sensor may track the overall expansion and contraction of the patient's airway via the movement of the EM sensors placed on the body of the patient.

Depending on the location of the instrument within the patient's airway, the patient's respiration may also have another effect on the location of the instrument. That is, the length of the path traversed by the instrument within the luminal network may expand and contract along with the respiratory cycle. Since the length of the instrument may not appreciably change during the procedure, the relative position of the instrument with respect to the luminal network may change as the overall length of luminal network defined by the path taken by the instrument in the luminal network expands and contracts. From the reference point of the distal end of the instrument, this may appear as though the instrument is being advanced and retraced within the luminal network even though the instrument is not being actively driven. In certain circumstances, the instrument may be substantially stationary with respect to the reference point of the platform even while from the reference point of the distal end of the instrument, the instrument is being advanced and retraced. In this case, the location of the instrument determined based on the EM sensor may indicate that the instrument is substantially stationary, the location of the instrument with respect to the reference frame of the luminal network may be changing in accordance with the patient's respiratory cycle.

Thus, certain aspects of this disclosure may relate to the detection of movement of the instrument with respect to the reference frame of the luminal network (e.g., movement of the luminal network around the instrument) due to a patient's respiration (or other physiological motion). Once detected, the robotic system may provide a user interface alert to indicate that there may be a certain amount of uncompensated error in the displayed location of the instrument.

VII. A. Overview of Image-Based Detection of Physiological Noise

Figure 12:
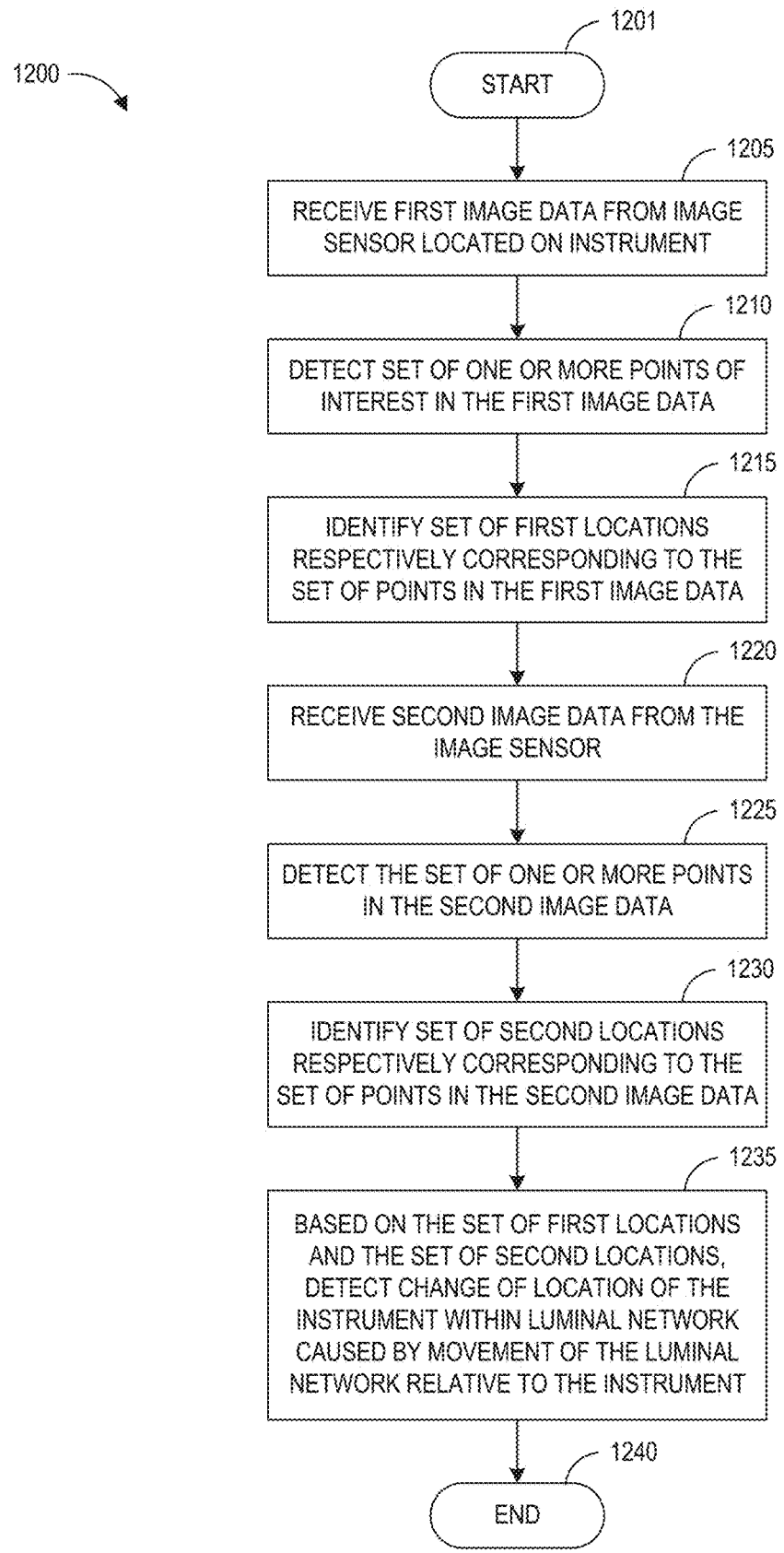
FIG. 12 is a flowchart illustrating an example method operable by a robotic system, or component(s) thereof, for detecting physiological noise in accordance with aspects of this disclosure.

FIG. 12 is a flowchart illustrating an example method operable by a robotic system, or component(s) thereof, for detecting physiological noise in accordance with aspects of this disclosure. For example, the steps of method 1200 illustrated in FIG. 12 may be performed by processor(s) and/or other component(s) of a medical robotic system (e.g., surgical robotic system 500) or associated system(s) (e.g., the image-based algorithm module 960 of the navigation configuration system 900). For convenience, the method 1200 is described as performed by the navigation configuration system, also referred to simply as the "system" in connection with the description of the method 1200.

The method 1200 begins at block 1201. At block 1205, the system may receive first image data from an image sensor located on an instrument, the instrument configured to be driven through a luminal network of a patient. In example embodiments, the instrument may comprise a bronchoscope configured to be driven through a patient's airways. In these embodiments, the system may be configured to detect respiratory motion of the instrument based at least in part on the images received from the image sensor.

At block 1210, the system may detect a set of one or more points of interest the first image data. As discussed above, the points of interest may be any distinguishable data across multiple image data, such as, for example, one or more identifiable pixels within the image or one or more objects detected in the image data. In certain embodiments, the points of interest may comprise a set of one or more pixels which can be detected over a sequence of one or more images. In some implementations, the detected object may comprise one or more distinguishable objects detected using image processing techniques of the related art, such as SURF and SIFT. However, any technique which can reliably detect and track one or more pixels through a series of images can be used to detect the points of interest which can be used in the image processing techniques described herein.

At block 1215, the system may identify a set of first locations respectively corresponding to the set of points in the first image data. In embodiments where the set of points correspond to identifiable pixels within the image, the set of locations may correspond to the row and/or column values of the pixels within the image. Thus, the first set of locations may comprise the X- and Y-coordinates for each of the pixels in the set of points.

At block 1220, the system may receive second image data from the image sensor. The second image may be an image received from the image sensor at a point in time occurring after the time at which the first image was captured by the image sensor.

At block 1225, the system may detect the set of one or more points in the second image data. The set of points detected in the second image may correspond to the set of points detected in the first image. The detection of the same set of points between multiple images will be described in greater detail below in connection with FIGS. 13A-13C.

At block 1230, the system may identify a set of second locations respectively corresponding to the set of points in the second image data. In some situations, when the physiological noise is affecting the relative position of the instrument with respect to the luminal network, the set of locations of the points of interest in the second image may be different from the set of locations of the points of interest in the first image. For example, as the instrument is advanced into the luminal network (e.g., due to contraction of the length of the luminal network), an object appearing in the images captured by the image sensor may appear as though it is approaching the image sensor. Thus, by tracking the location of the object (e.g., by tracking the points of interest), the system may be able to estimate motion of the instrument with respect to the luminal network.

At block 1235, the system may, based on the set of first locations and the set of second locations, detect a change of location of the luminal network around the instrument caused by movement of the luminal network relative to the instrument. As described above, movement of the location of the tracked points of interest may be indicative of movement of the luminal network with respect to the instrument. Specific embodiments related to the detection of the change of location caused by movement of the luminal network will be described below in connection with FIGS. 14A-15B. The method 1200 ends at block 1240.

Figure 13B:
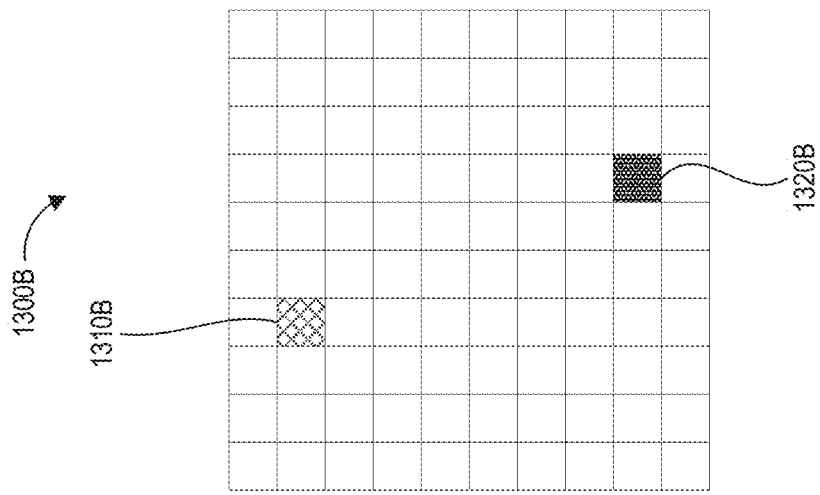
FIG. 13B illustrates another example of image data captured by an image sensor at a second point in time, after the first point in time, in accordance with aspects of this disclosure.
Figure 13A:
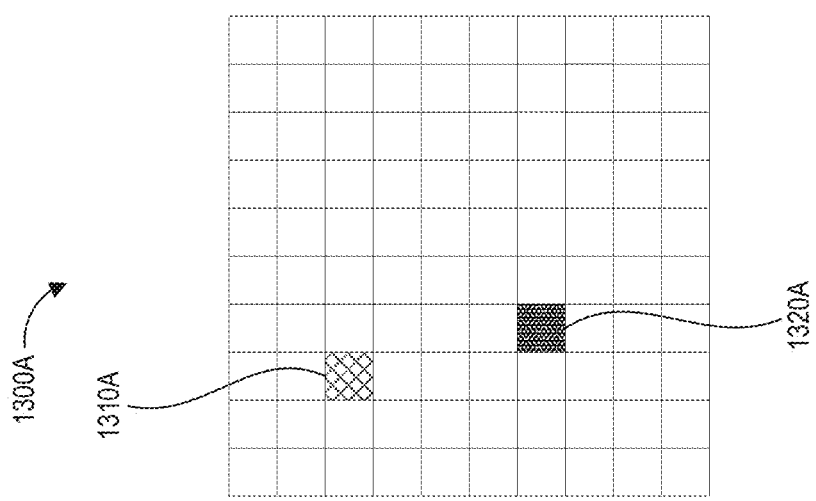
FIG. 13A illustrates example image data captured by an image sensor at a first point in time in accordance with aspects of this disclosure.
Figure 13D:
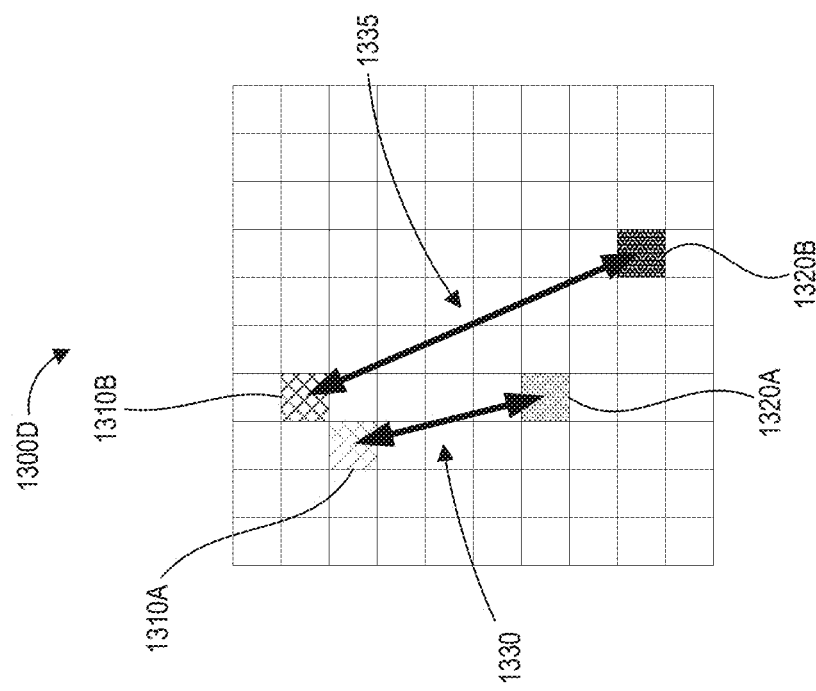
FIG. 13D illustrates another example of the change in location of example pixels between the image data frames illustrated in FIGS. 13A-13B in accordance with aspects of this disclosure.
Figure 13C:
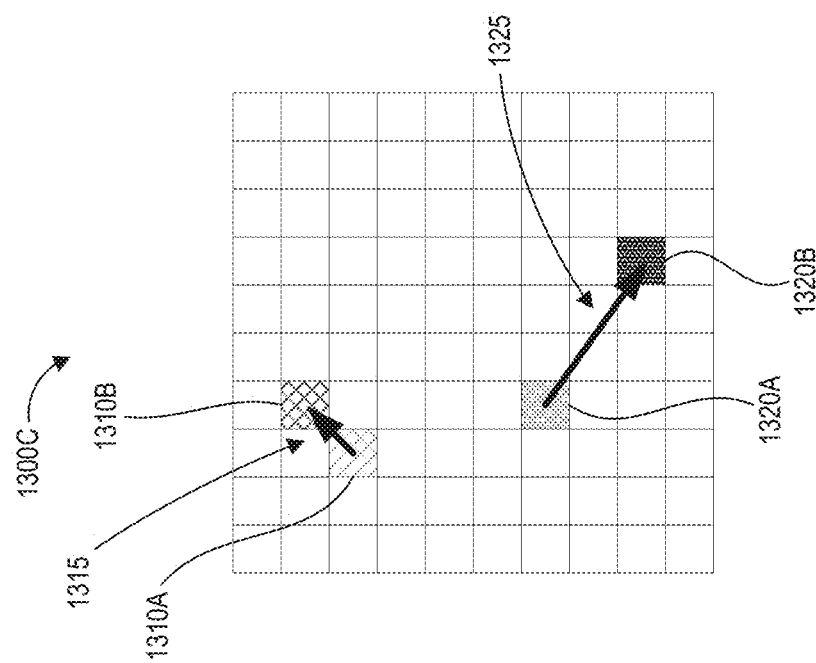
FIG. 13C illustrates an example of the change in location of example pixels between the image data frames illustrated in FIGS. 13A-13B in accordance with aspects of this disclosure.

VII. B. Example of Tracking Points of Interest Between a Series of Image Data Frames FIG. 13A illustrates example image data captured by an image sensor at a first point in time in accordance with aspects of this disclosure. FIG. 13B illustrates another example of image data captured by an image sensor at a second point in time, after the first point in time, in accordance with aspects of this disclosure. Depending on the embodiment, the first image data and the second image data may be successive images in a series of image data frames captured by the image sensor or may be separated in time with at least one additional image data frame interposed therebetween. FIG. 13C illustrates an example of the change in location of example pixels between the image data frames illustrated in FIGS. 13A-13B in accordance with aspects of this disclosure. FIG. 13D illustrates another example of the change in location of example pixels between the image data frames illustrated in FIGS. 13A-13B in accordance with aspects of this disclosure.

The image data frames illustrated in FIGS. 13A-13B are simplified to show certain aspects of the detected image data which may be involved in the tracking of the locations of points of interest between a series of image data frames. In certain embodiments, the image data captured by an image sensor of an instrument may include an array of pixels having a greater or lesser number of pixels than illustrated. For example, the image sensor may be configured to capture 200×200 pixel image data frames in certain implementations.

FIG. 13A illustrates first image data 1300A including two points of interest 1310A and 1320A. The limited number of points of interest 1310A and 1320A is simplified merely for descriptive purposes and, in other embodiments, a larger number of points of interest 1310A and 1320A may be detected and tracked in the first image data 1300A. Further, in the FIG. 13A example, the points of interest 1310A and 1320A may correspond to individual pixels within the first image data 1300A. However, as discussed above, in other embodiments the points of interest 1310A and 1320A may correspond to objects identified by the object detection module 964 or points of interest detected using image processing techniques such as SURF and/or SIFT.

In the second image data 1300B of FIG. 13B, the system may detect the same points of interest 1310B and 1320B which were identified in the first image data 1300A. However, the points of interest 1310B and 1320B may have moved to new locations within the second image data 1300B in the time elapsed between the capturing of the first and second image data 1300A and 1300B. The movement of the points of interest 1310B and 1320B from the first image data 1300A to their respective locations in the second image data 1300B may be based on the relative movement of the corresponding portions of the luminal network with respect to the location of the image sensor. When the instrument is stationary with respect to the robotic system (e.g., when no robotic commands are being provided to drive the instrument), the system may be able to infer that movement of the points of interest 1310B and 1320B, and thus instrument within the luminal network, is due physiological noise. In a bronchoscopy example, the physiological noise may correspond to the length of the luminal network expanding and contracting along the path taken by the instrument due to respiration of the patient. Additionally or alternatively, the change in the diameter of the airway due to respiration may also be tracked by changes in the locations of the points of interest. Examples of physiological noise which may be detected by the image methodologies disclosed herein include respiration of the patient and a heart rate of the patient.

The locations of the points of interest in FIGS. 13A-14B may include information 911 (e.g., see FIG. 10A) such as the 2D locations of the points within the first image data and the second image data. Thus, the locations of the points of interest may include the X- and Y-coordinates for each of the points. In other embodiments, the system may track information 911 such as the location of the points in 3D space (not illustrated) based on the image data 1300A and 1300B. In these embodiments, the system may extract depth information from the each of the image data 1300A and 1300B and represent the location of the points in 3D information 911 indicative of the respective locations of the points.

FIG. 13C illustrates the locations of the points of interest at each of the first point in time and the second point in time overlaid on the same image data frame. As shown in FIG. 13C, a first point of interest 1310A and 1310B moved from the first image data 1300A to different location in the second image data 1300B. The movement of the first point of interest is illustrated by the vector 1315. Similarly, a second point of interest 1320A and 1320B has moved between the first and second image data 1300A and 1300B as illustrated by the vector 1325.

In more general terms, the system may track a set of points of interest over a series of image data frames received from an image sensor positions on the instrument. The system may determine a "scale change" between two successive image data frames in the series. FIG. 13D illustrates another example of the locations of the points of interest at each of the first point in time and the second point in time overlaid on the same image data to illustrate the relative distances between the points of interest. As shown in FIG. 13D, a first point of interest 1310A and 1310B moved from the first image data 1300A to different location in the second image data 1300B. The system may determine a determine a first distance 1330 between the first point 1310A and the second point 1320A in the first image data based on the locations of the first point 1310A and the second point 1320A in the first image data 1300A. The system may also determine a second distance 1335 between the first point 1310B and the second point 1320B in the second image data 1300B based on the locations of the first point 1310B and the second point 1320B in the first image data 1300B. In some implementations, the first and second distances 1330 and 1335 distance may be determined by the Euclidean distance between the respective points.

The system may use the first distance 1330 and the second distance 1335 to detect the change of location of the instrument within the luminal network. For example, in one embodiment, the system may determine a scale change estimate based on the first distance 1330 and the second distance 1335. In one implementation, the scale change estimate may be based on the difference between the first distance 1330 and the second distance 1335.

Although only two points of interest are illustrated in FIGS. 13A-13D, the system may track a set of at least three points of interest over the series of image data frames. When the number of points in the set of points of interest is less than the number of pixels in the image data, the set of points may be considered a "sparse" set of points. In other embodiments, the number of points in the set of points of interest tracked by the system may be a "dense" set of points, where the number of tracked points is equal to the number of pixels in the image data. The system may group the points in the set of points a plurality of pairs of points. This may include each combination of pairs of points for the entire set of points or may include a subset of the possible pairs of points for the set of points.

The system may determine a scale change value between the two image data frames based on the scale estimates determined for the pairs of points. In certain embodiments, the scale change value may be representative of the scale change between the two image data frames based on all or a subset of the tracked pairs of points. In one embodiment, the system may determine the scale change value as a median value of the scale change estimates. In another embodiment, the system may determine the scale change value as an average value of the scale change estimates. Those skilled in the art will recognize that other techniques or methodologies may be used to generate a scale change value based on the set of scale change estimates.

Figure 15A:
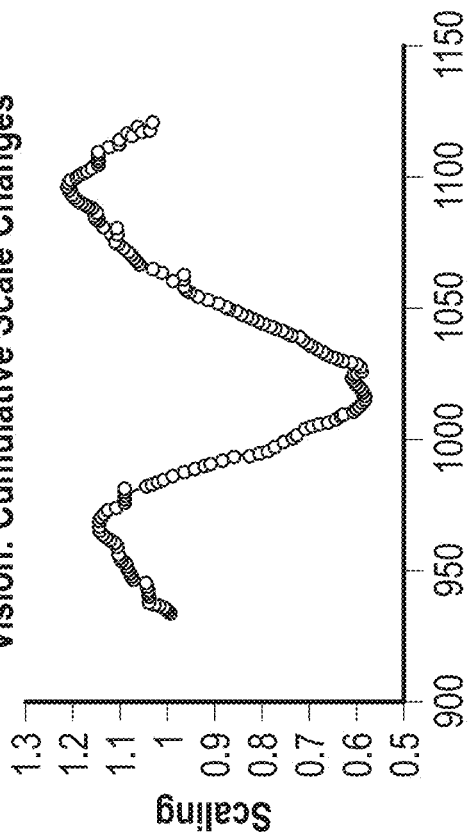
FIGS. 15A-15B are graphs which illustrate the changes to an accumulated scale change value over a sequence of image data frames in accordance with aspects of this disclosure.
Figure 15B:
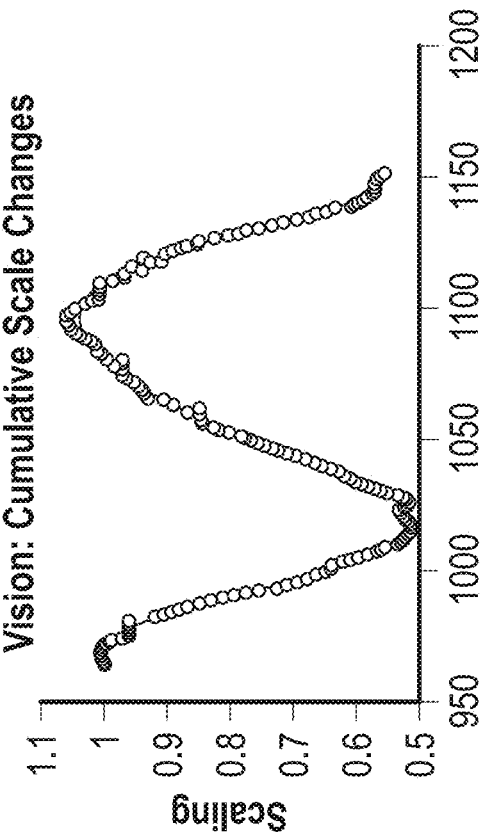
Figure 14A:
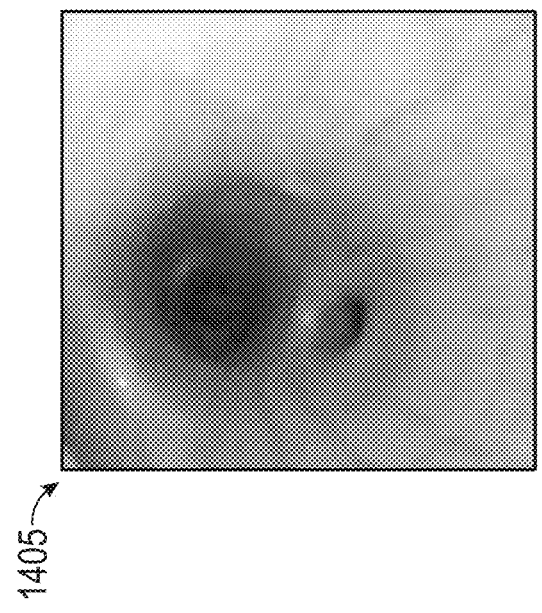
FIGS. 14A-14B illustrate an example of two image data frames within a sequence of image data frames for which the scale change value may be accumulated in accordance with aspects of this disclosure.
Figure 14B:
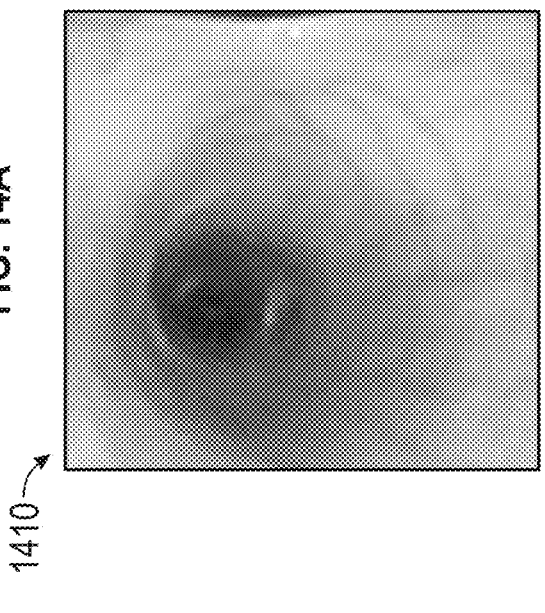

VII. C. Example of Tracking a Cumulative Scale Change Over a Series of Image Data Frames The system may accumulate a scale change value over a sequence of image data frames, and there by track the scale change over more than two image data frames. In certain implementations, the system may accumulate the scale change value my multiplying the scale change values between successive pairs of image data frames in the sequence of image data frames. FIGS. 14A-14B illustrate an example of two image data frames within a sequence of image data frames for which the scale change value may be accumulated in accordance with aspects of this disclosure. FIGS. 15A-15B are graphs which illustrate the changes to an accumulated scale change value over a sequence of image data frames in accordance with aspects of this disclosure.

With reference to FIGS. 14A-15B, a sequence of image data is illustrated over a numbered sequence of image data frames, where FIG. 15A includes image data from frame #930 to frame #1125 and FIG. 15B includes image data from frame #965 to frame #1155. FIG. 14A includes image data 1405 from frame #1125 while FIG. 14B includes image data 1410 from frame #1155.

Each of FIGS. 15A-15B illustrates cumulative scale values determined in accordance with aspects of this disclosure. For example, the values at each frame in the graphs may be calculated by multiplying a currently determined scale change value between two image data frames with the accumulated scale change value determined for the previous frame. As is shown the graphs, the cumulative scale change values are period when periodic physiological noise is affecting the position of the image sensor (and thus the distal end of the instrument). The system may track cumulative changes to the scale change value in the sequence of image data received from the image sensor over a first time period and determine the frequency of the physiological noise based on the cumulative scale change values over a period of time. In one embodiment, the system may transform the tracked scale change value into a frequency domain (e.g., using a Fourier or other transform). The system may further identify at least one harmonic in the tracked scale change value in frequency domain. In certain embodiments, the system may identify the first harmonic in the tracked scale change value in frequency domain as an estimated frequency of the physiological noise.

The frequency determined from the cumulative scale change values may be utilized as an estimate of the frequency of physiological noise. However, physiological noise may not always have a large enough effect on the location of the instrument with respect to the luminal network that the physiological noise will introduce error in the localization of the instrument (e.g., as determined by the navigation configuration system 900). Thus, in certain embodiments, the system may compare the estimated frequency of the physiological noise to a separately estimated frequency of the physiological noise.

In one embodiment, the system may determine a first physiological movement frequency of the patient based on a sequence of image data frames received from the image sensor. The system may further determine a second physiological movement frequency of the patient based on the data received from one or more location sensors (e.g., an EM sensor, a shape-sensing fiber, robot command data, and a radiation-based image sensors). Examples of systems and techniques for determining a physiological movement frequency of a patient based on data received from one or more location sensors is described in U.S. Patent Application Pub. No. 2018/0279852, filed on Mar. 29, 2018, the entirety of which is incorporated herein by reference.

The system may then determine whether the difference between the first physiological movement frequency based on the sequence of image data and the second physiological movement frequency based on the location sensor data is less than a threshold difference. When the difference between the first and second physiological movement frequencies is less than the threshold difference, the system may determine that the frequency of the scale changes in the sequence of image data frames is due to a physiological noise source. In certain embodiments, the system may provide an indication of the detected change of location of the instrument within the luminal network to a display in response to determining that the frequency of the scale changes in the sequence of image data frames is due to a physiological noise source.

In contrast, when the difference between the first and second physiological movement frequencies is not less than the threshold difference, the system may not have sufficient confidence to determine that the movement in the luminal network with respect to the instrument will affect the accuracy of the in the localization of the instrument (e.g., as determined by the navigation configuration system 900). In other words, when the frequency of the scale changes in the sequence of image data does not sufficiently match the physiological frequency measured using a separate technique, the system may infer that the location of the instrument sufficiently stable with respect to the luminal network so as to not introduce errors into the localization of the instrument.

VII. D. Example of Backtracking of Points of Interest

Depending on the particular image processing technique used to identify the points of interest (e.g., SURF, SIFT, etc.), the order in which two frames of image data are processed may affect the identification of the locations of the points of interest within the image data. For example, referring to FIGS. 13A-13B, in one example, the system may identify pixels 1310B and 1320B in image data frame 1300B by tracking a change in the location of pixels 1310A and 1320A from frame 1300A. However, under certain conditions, in reversing this process by backtracking pixels 1310B and 1320B from image data frame 1300B to image data frame 1300A, the system may identify different pixels from the original pixels 1310A and 1320A. When pixels identified during a backtracking process are not the same as the original pixels 1310A and 1320A, the identified pixels may not be sufficiently robust to determine a scale change estimate.

Accordingly, the system may identify a set of backtracked locations of the set of points in first image data via backtracking the set of points from second image data to the first image data and compare the set of backtracked locations to the original set of locations of the set of points identified from the first image data. The system may identify a sub-set of the points from the set of points for which the backtracked locations are not within a threshold distance of the set of first locations (e.g., the locations of the backtracked pixels do not sufficiently match the originally determined locations of the pixels used for forward tracking). The system may remove the sub-set of points from the set of points and determine the scale change estimate without the removed sub-set of points. This may improve the accuracy and robustness of the point tracking over a series of image data frames.

VII. D. Example of Detecting Physiological Noise During Dynamic Instrument Movement While certain aspects of this disclosure may be performed while the instrument is stationary (e.g., while no robot commands are provided to move the instrument), it may also be desirable to detect physiological noise during dynamic instrument movement (e.g., while driving the instrument within the luminal network). During such dynamic instrument movement, the change between two image data frames (e.g., received at a first time and a second time), may be the result of a combination of instrument movement and physiological noise. Accordingly, to detect the physiological noise during dynamic movement of the instrument, the instrument movement motion should be decoupled from the physiological noise in the motion detected by the image-based algorithm module 970. In certain embodiments, the system can perform motion decoupling in 3D space by using the 3D movement of the instrument received from positioning sensors (e.g., EM-based state data, robot-based state data, EM and/or optical shape sensing state data, etc.). The system can employ certain image processing techniques including image-based 3D motion estimation (e.g., structure from motion) to determine the relative 3D motion between the instrument and the luminal network.

In one example implementation, the system may determine a location sensor-based 3D instrument movement between two points in time (e.g., between $t_0$ and $t_1$) based on data received from locations sensors. The 3D instrument movement data may be represented by three spatial degrees-of-freedom (DoF), for example $\{x_z, y_z, z_z\}$, and three rotational DoF, for example, $\{\theta_s^x, \theta_s^y, \theta_s^z\}$. The system may also determine an image sensor-based 3D instrument movement between the two points in time represented by the same six DoF measurements as in the location sensor-based 3D instrument movement.

The system may determine a 3D instrument movement estimate representative of physiological movement by determining the difference between the location sensor-based 3D instrument movement and the image sensor-based 3D instrument movement. The system may then accumulate the 3D instrument movement estimate representative of physiological movement over a sequence of image data and location sensor measurements over a given time period, from which a frequency and amplitude associated with the physiological noise can be extracted (e.g., using one or more of the above-defined techniques including harmonic analysis).

VII. E. Example of Detecting an Instrument Transitioning Between Junctions Due to Physiological Noise There may be uncertainty in the determined location of an instrument introduced due to physiological noise when the instrument is located near a junction in a luminal network (e.g., when a current segment branches into two or more child segments). That is, if the instrument is not located near a junction, even though the instrument may have a change in depth within a current segment due to the physiological noise, the instrument may remain within the current segment without transitioning into another segment. However, if the instrument is located near a junction, the movement of the instrument due to physiological noise may be sufficient to move the instrument from one segment into another segment. Thus, it may be desirable to provide an indication to the user that the system is unable to accurately determine whether the instrument has crossed over the junction into a new segment of the luminal network.

In certain embodiments, the system can detect junction transition by identifying and analyzing the airways from image data received from an image sensor. For example, the system tracks the locations of detected airways between two image data frames (e.g., received at a first time $t_0$ and a second time $t_1$). The system may, in certain embodiments, determine that the instrument has transitioned through a junction in response to at least one of the following conditions being satisfied: 1) all of the estimated airways overlap with the detected airways in the image data at time $t_1$, but there exists one or more detected airways in the image data at time $t_1$ that do not have an overlap with the estimated airways; 2) all the detected airways in in the image data at time $t_1$ overlap with the estimated airways, but there exists one or more estimated airways do not have an overlap with the detected airways the image data at time $t_0$; and 3) there exists one or more detected airways that do not overlap with the estimated airways and there exists one or more estimated airways do not overlap with the detected airways. As such, embodiments may track the location and sizes of prior airways and compare them to the locations and sizes of airways detected in current image data. The presences of one or more of the above listed conditions and the detected of movement of the anatomy relative to the instrument may be used by the system to detect a transition between junctions.

VIII. Implementing Systems and Terminology

Implementations disclosed herein provide systems, methods and apparatuses for detecting physiological noise during navigation of a luminal network.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The path-based navigational functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical robotic system, comprising:
a set of one or more processors; and
at least one computer-readable memory in communication with the set of processors and having stored thereon computer-executable instructions to cause the set of processors to:
receive first image data from an image sensor located on an instrument, the instrument configured to be driven through a luminal network of a patient,
determine a first position of the instrument within the luminal network based on data received from at least one location sensor,
detect a set of one or more points of interest the first image data,
identify a set of first locations respectively corresponding to the set of one or more points in the first image data,
receive second image data from the image sensor,
detect the set of one or more points in the second image data,
identify a set of second locations respectively corresponding to the set of one or more points in the second image data,
determine that the instrument is not actively being driven based on robotic commands not being provided to drive the instrument,
based on the set of first locations and the set of second locations and in response to determining that the instrument is not actively being driven, detect a change of position of the instrument within the luminal network caused by movement of the luminal network relative to the instrument, and
generate, in response to the detecting of the change of the position, an alert indicative of uncompensated error in the determined first position of the instrument due to the movement of the luminal network relative to the instrument.

2. The system of claim 1, wherein:
the set of first locations and the set of second locations respectively define two-dimensional (2D) locations of the set of one or more points within the first image data and the second image data.

3. The system of claim 2, wherein:
the set of one or more points comprises four or more points, and
the memory further has stored thereon computer-executable instructions to cause the set of processors to:
group the set of four or more points into a plurality of pairs of points, a first pair of points comprising a first point and a second point,
determine a first distance between the first point and the second point in the first image data based on the set of first locations, and
determine a second distance between the first point and the second point in the second image data based on the set of second locations,
wherein detecting the change of position of the instrument within the luminal network is further based on the first distance and the second distance.

4. The system of claim 3, wherein the memory further has stored thereon computer-executable instructions to cause the set of processors to:
determine a first scale change estimate for the first pair of points based on the first distance and the second distance, and
determine a scale change value representative of a scale change between the first image data and the second image data based on the scale change estimate,
wherein detecting the change of position of the instrument within the luminal network is further based on the scale change value.

5. The system of claim 4, wherein the memory further has stored thereon computer-executable instructions to cause the set of processors to:
determine a set of scale change estimates respectively corresponding to the plurality of pairs of points, and
determine the scale change value based on a median value of the set of scale change estimates or an average value of the set of scale change estimates.

6. The system of claim 1, wherein the memory further has stored thereon computer-executable instructions to cause the set of processors to:
track cumulative changes to a scale change value representative of a scale change in image data received from the image sensor over a first time period,
transform the tracked scale change value into a frequency domain, and
identify at least one harmonic in the tracked scale change value in the frequency domain,
wherein detecting the change of position of the instrument within the luminal network is further based on the at least one harmonic.

7. The system of claim 1, wherein the memory further has stored thereon computer-executable instructions to cause the set of processors to:
determine a first physiological movement frequency of the patient based on the set of first locations and the set of second locations, wherein detecting the change of position of the instrument within the luminal network is further based on the first physiological movement frequency, and
provide an indication of the detected change of position of the instrument within the luminal network to a display.

8. The system of claim 7, wherein the memory further has stored thereon computer-executable instructions to cause the set of processors to:
determine a second physiological movement frequency of the patient based on the data received from the at least one location sensor, and
determine that a difference between the first physiological movement frequency and the second physiological movement frequency is less than a threshold difference,
wherein detecting the change of position of the instrument within the luminal network is further in response to determining that the difference between the first physiological movement frequency and the second physiological movement frequency is less than the threshold difference.

9. The system of claim 7, wherein the at least one location sensor comprises at least one of: an electromagnetic (EM) sensor, a shape-sensing fiber, robot command data, and a radiation-based image sensor.

10. The system of claim 7, wherein the physiological movement comprises at least one of a respiration of the patient or a heart rate of the patient.

11. The system of claim 1, wherein the memory further has stored thereon computer-executable instructions to cause the set of processors to:
   identify a set of backtracked locations of the set of one or more points in the first image data via backtracking the set of one or more points from the second image data to the first image data,
   compare the set of backtracked locations to the set of first locations,
   identify a sub-set of one or more points in the set of one or more points for which the backtracked locations are not within a threshold distance of the set of first locations, and
   remove the sub-set of one or more points from the set of one or more points.

12. The system of claim 1, wherein the set of first locations and the set of second locations comprise two-dimensional (2D) information indicative of the respective locations of the set of one or more points with respect to a coordinate system of the first image data and the second image data.

13. The system of claim 1, wherein the memory further has stored thereon computer-executable instructions to cause the set of processors to:
   extract depth information for the set of one or more points in the first image data, and
   extract depth information for the set of one or more points in the second image data,
   wherein the set of first locations and the set of second locations comprise three-dimensional (3D) information indicative of the respective locations of the set of one or more points determined based on depth information extracted from each of the first image data and second image data.

14. A non-transitory computer readable storage medium having stored thereon instructions that, when executed, cause at least one computing device to:
   receive first image data from an image sensor located on an instrument, the instrument configured to be driven through a luminal network of a patient;
   determine a first position of the instrument within the luminal network based on data received from at least one location sensor;
   detect a set of one or more points of interest in the first image data;
   identify a set of first locations respectively corresponding to the set of one or more points in the first image data;
   receive second image data from the image sensor;
   detect the set of one or more points in the second image data;
   identify a set of second locations respectively corresponding to the set of one or more points in the second image data;
   determine that the instrument is not actively being driven based on robotic commands not being provided to drive the instrument;
   based on the set of first locations and the set of second locations, detect a change of position of the instrument within the luminal network caused by movement of the luminal network relative to the instrument; and
   generate, in response to the detecting of the change of the position, an alert indicative of uncompensated error in the determined first position of the instrument due to the movement of the luminal network relative to the instrument.

15. The non-transitory computer readable storage medium of claim 14, wherein:
   the set of first locations and the set of second locations respectively define two-dimensional (2D) locations of the set of one or more points within the first image data and the second image data.

16. The non-transitory computer readable storage medium of claim 15, wherein:
   the set of one or more points comprises four or more points, and
   the non-transitory computer readable storage medium further has stored thereon instructions that, when executed, cause the at least one computing device to:
      group the set of four or more points into a plurality of pairs of points, a first pair of points comprising a first point and a second point;
      determine a first distance between the first point and the second point in the first image data based on the set of first locations; and
      determine a second distance between the first point and the second point in the second image data based on the set of second locations,
      wherein detecting the change of position of the instrument within the luminal network is further based on the first distance and the second distance.

17. The non-transitory computer readable storage medium of claim 16, wherein the non-transitory computer readable storage medium further has stored thereon instructions that, when executed, cause the at least one computing device to:
   determine a first scale change estimate for the first pair of points based on the first distance and the second distance; and
   determine a scale change value representative of a scale change between the first image data and the second image data based on the scale change estimate,
   wherein detecting the change of position of the instrument within the luminal network is further based on the scale change value.

18. The non-transitory computer readable storage medium of claim 17, wherein the non-transitory computer readable storage medium further has stored thereon instructions that, when executed, cause the at least one computing device to:
   determine a set of scale change estimates respectively corresponding to the plurality of pairs of points; and
   determine the scale change value based on a median value of the set of scale change estimates or an average value of the set of scale change estimates.

19. The non-transitory computer readable storage medium of claim 14, wherein the non-transitory computer readable storage medium further has stored thereon instructions that, when executed, cause the at least one computing device to:
   track cumulative changes to a scale change value representative of a scale change in image data received from the image sensor over a first time period;
   transform the tracked scale change value into a frequency domain; and
   identify at least one harmonic in the tracked scale change value in the frequency domain, wherein detecting the change of position of the instrument within the luminal network is further based on the at least one harmonic.

20. The non-transitory computer readable storage medium of claim 14, wherein the non-transitory computer readable storage medium further has stored thereon instructions that, when executed, cause the at least one computing device to:
   determine a first physiological movement frequency of the patient based on the set of first locations and the set of second locations, wherein detecting the change of position of the instrument within the luminal network is further based on the first physiological movement frequency; and
   provide an indication of the detected change of position of the instrument within the luminal network to a display.

21. The non-transitory computer readable storage medium of claim 20, wherein the non-transitory computer readable storage medium further has stored thereon instructions that, when executed, cause the at least one computing device to:
   determine a second physiological movement frequency of the patient based on the data received from the at least one location sensor; and
   determine that a difference between the first physiological movement frequency and the second physiological movement frequency is less than a threshold difference,
   wherein detecting the change of position of the instrument within the luminal network is further in response to determining that the difference between the first physiological movement frequency and the second physiological movement frequency is less than the threshold difference.

22. The non-transitory computer readable storage medium of claim 20, wherein the physiological movement comprises at least one of a respiration of the patient or a heart rate of the patient.

23. The non-transitory computer readable storage medium of claim 14, wherein the non-transitory computer readable storage medium further has stored thereon instructions that, when executed, cause the at least one computing device to:
   extract depth information for the set of one or more points in the first image data; and
   extract depth information for the set of one or more points in the second image data,
   wherein the set of first locations and the set of second locations comprise three-dimensional (3D) information indicative of the respective locations of the set of one or more points determined based on depth information extracted from each of the first image data and second image data.

24. A method for detecting a change of position of an instrument, comprising:
   receiving first image data from an image sensor located on the instrument, the instrument configured to be driven through a luminal network of a patient;
   determining a first position of the instrument within the luminal network based on data received from at least one location sensor;
   detecting a set of one or more points of interest in the first image data;
   identifying a set of first locations respectively corresponding to the set of one or more points in the first image data;
   receiving second image data from the image sensor;
   detecting the set of one or more points in the second image data;
   identifying a set of second locations respectively corresponding to the set of one or more points in the second image data;
   determining that the instrument is not actively being driven based on robotic commands not being provided to drive the instrument;
   based on the set of first locations and the set of second locations, detecting the change of position of the instrument within the luminal network caused by movement of the luminal network relative to the instrument; and
   generating, in response to the detecting of the change of the position, an alert indicative of uncompensated error in the determined first position of the instrument due to the movement of the luminal network relative to the instrument.

25. The method of claim 24, wherein:
the set of first locations and the set of second locations respectively define two-dimensional (2D) locations of the set of one or more points within the first image data and the second image data.

26. The method of claim 25, wherein:
the set of one or more points comprises four or more points, and
the method further comprises:
   grouping the set of four or more points into a plurality of pairs of points, a first pair of points comprising a first point and a second point;
   determining a first distance between the first point and the second point in the first image data based on the set of first locations; and
   determining a second distance between the first point and the second point in the second image data based on the set of second locations,
   wherein detecting the change of position of the instrument within the luminal network is further based on the first distance and the second distance.

27. The method of claim 26, further comprising:
determining a first scale change estimate for the first pair of points based on the first distance and the second distance; and
determining a scale change value representative of the scale change between the first image data and the second image data based on the scale change estimate,
wherein detecting the change of position of the instrument within the luminal network is further based on the scale change value.

28. The method of claim 27, further comprising:
determining a set of scale change estimates respectively corresponding to the plurality of pairs of points; and
determining the scale change value based on a median value of the set of scale change estimates or an average value of the set of scale change estimates.

29. The method of claim 24, further comprising:
tracking cumulative changes to a scale change value representative of a scale change in image data received from the image sensor over a first time period;
transforming the tracked scale change value into a frequency domain; and
identifying at least one harmonic in the tracked scale change value in the frequency domain,
wherein detecting the change of position of the instrument within the luminal network is further based on the at least one harmonic.

30. The method of claim 24, further comprising:
determining a first physiological movement frequency of the patient based on the set of first locations and the set of second locations, wherein detecting the change of position of the instrument within the luminal network is further based on the first physiological movement frequency; and providing an indication of the detected change of position of the instrument within the luminal network to a display.

* * * * *